(12) United States Patent
Shepard et al.

(10) Patent No.: US 9,663,827 B2
(45) Date of Patent: May 30, 2017

(54) MOLECULAR GRAM STAIN

(71) Applicant: AdvanDx, Inc., Woburn, MA (US)

(72) Inventors: Janeen R. Shepard, Wilmington, MA (US); Mark Fiandaca, Princeton, MA (US); Henrik Stender, Gentofte (DK)

(73) Assignee: AdvanDx, Inc., Woburn, MA (US)

( * ) Notice: Subject to any disclaimer, the term of this patent is extended or adjusted under 35 U.S.C. 154(b) by 0 days.

(21) Appl. No.: 14/043,040

(22) Filed: Oct. 1, 2013

(65) Prior Publication Data
US 2014/0121287 A1 May 1, 2014

Related U.S. Application Data

(63) Continuation of application No. PCT/US2012/031454, filed on Mar. 30, 2012.

(60) Provisional application No. 61/470,661, filed on Apr. 1, 2011.

(51) Int. Cl.
*C12Q 1/68* (2006.01)

(52) U.S. Cl.
CPC ......... *C12Q 1/689* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,985,563 A * | 11/1999 | Hyldig-Nielsen et al. | 435/6.12 |
| 6,485,901 B1 * | 11/2002 | Gildea | C07K 14/003 435/5 |
| 2001/0010910 A1 | 8/2001 | Hyldig-Nielsen et al. | |
| 2002/0090626 A1 * | 7/2002 | Hyldig-Nielsen | C12O 1/689 435/6.15 |
| 2003/0077601 A1 | 4/2003 | Ebersole et al. | |
| 2004/0038307 A1 * | 2/2004 | Lee et al. | 435/7.1 |
| 2004/0110138 A1 | 6/2004 | Lem et al. | |
| 2007/0042354 A1 | 2/2007 | Engelhard | |
| 2009/0246758 A1 * | 10/2009 | Fiandaca | C07K 14/003 435/6.12 |
| 2009/0286691 A1 * | 11/2009 | Kim | C12Q 1/689 506/9 |

FOREIGN PATENT DOCUMENTS

| | | | | |
|---|---|---|---|---|
| EP | 1770171 A1 | | 4/2007 | |
| EP | WO2007039319 | * | 4/2007 | C12Q 1/68 |
| WO | WO-2004/044247 A2 | | 5/2004 | |
| WO | WO-2007/083852 A1 | | 7/2007 | |
| WO | WO 2008/041960 A2 | | 4/2008 | |
| WO | WO-2008/104122 A1 | | 9/2008 | |

OTHER PUBLICATIONS

Brehm-Stecher BF, Hyldig-Nielsen JJ, Johnson EA. Design and evaluation of 16S rRNA-targeted peptide nucleic acid probes for whole-cell detection of members of the genus *Listeria*. Appl Environ Microbiol. Sep. 2005; 71(9):5451-7.*
Genbank Accession No. U18766—Helicobacter bilis 16S rRNA gene, partial sequence (GI: 47524191, submitted on May 20, 2004, retrieved on May 12, 2016 from http://www.ncbi.nlm.nih.gov/nuccore/U18766).*
Genbank Accession No. X68417—*S. aureus* gene 16S rRNA (GI: 312111, submitted by Ludwig et al. Sep. 8, 1992, retrieved on May 12, 2016 from http://www.ncbi.nlm.nih.gov/nuccore/X68417).*
Genbank Accession No. J01859—*E. coli* 16S rRNA (GI: 174375 submitted on Aug. 1995, retrieved on May 12, 2016 http://www.ncbi.nlm.nih.gov/nuccore/J01859).*
Genbank Accession No. AB036835—Enterococcus faecalis gene for 16S rRNA, complete sequence (GI: 12328427 submitted on Jan. 16, 2007, retrieved on May 12, 2016 http://www.ncbi.nlm.nih.gov/nuccore/ab036835).*
Kempf VA, Trebesius K, Autenrieth IB. Fluorescent in situ hybridization allows rapid identification of microorganisms in blood cultures. J Clin Microbiol. Feb. 2000; 38(2):830-8.*
Nadkarni MA, Martin FE, Jacques NA, Hunter N. Determination of bacterial load by real-time PCR using a broad-range (universal) probe and primers set. Microbiology. Jan. 2002; 148(Pt 1):257-66.*
Perry-O'Keefe H, Rigby S, Oliveira K, Sorensen D, Stender H, Coull J, Hyldig-Nielsen JJ. Identification of indicator microorganisms using a standardized PNA FISH method. J Microbiol Methods. Dec. 2001; 47(3):281-92.*
Morgan M, Marlowe E, Della-Latta P, Salimnia H, Novak-Weekley S, Wu F, Crystal BS: Multicenter evaluation of a new shortened peptide nucleic acid fluorescence in situ hybridization procedure for species identification of select Gram-negative bacilli from blood cultures. J Clin Microbiol 2010, 48(6):2268-2270.*
Stender H. PNA FISH: an intelligent stain for rapid diagnosis of infectious diseases. Expert Rev Mol Diagn. Sep. 2003; 3(5):649-55.*
Tang BM, McLean AS, Dawes IW, Huang SJ, Cowley MJ, Lin RC. Gene-expression profiling of gram-positive and gram-negative sepsis in critically ill patients. Crit Care Med. Apr. 2008; 36(4):1125-8.*
Wellinghausen N, Wirths B, Franz AR, Karolyi L, Marre R, Reischl U. Algorithm for the identification of bacterial pathogens in positive blood cultures by real-time LightCycler polymerase chain reaction (PCR) with sequence-specific probes. Diagn Microbiol Infect Dis. Apr. 2004; 48(4):229-41.*
Bentley et al., "Development of PCR-Based Hybridzation Protocol for Identification of *Streptococcal* Species," *J. Clin. Microbiol.*, Am. Soc. Microbiol., 33( 5):1296-1301 (1995).

(Continued)

*Primary Examiner* — Samuel Woolwine
*Assistant Examiner* — Olayinka Oyeyemi
(74) *Attorney, Agent, or Firm* — McCarter & English, LLP; Jonathan M. Sparks; Jin Wang, Esq.

(57) ABSTRACT

The present invention relates to peptide nucleic acid (PNA) probes, PNA probe sets and methods for the analysis of Gram positive and Gram negative organisms optionally present in a sample. The invention further relates to diagnostic kits comprising such PNA probes.

34 Claims, 1 Drawing Sheet

(56) References Cited

OTHER PUBLICATIONS

Drazenovich et al., "Detection of Rodent *Helicobacter* spp. By Use of Fluorogenic Nuclease Polymerase Chain Reaction Assays," *Comparative Medicine*, 52(4):347-353 (2002).
Pakarinen et al., "Proliferation of mycobacteria in a piggery environment revealed by mycobacterium-specific real-time quantitative PCR and 16S rRNA sandwich hybridization," *Vet. Microbiol.*, 120(1-2):105-112 (2007).
EBI database accession No. BD171778 (2003)—Ezaki, "Method for detecting microorganisms, and primer set for detecting microorganisms".

\* cited by examiner

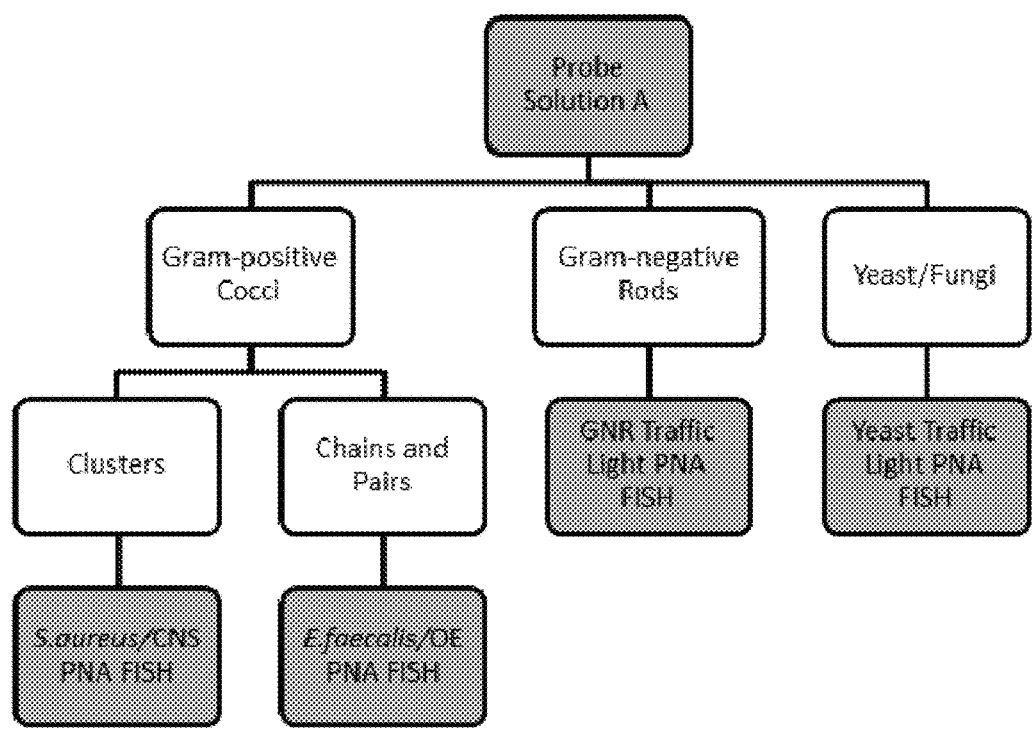

MOLECULAR GRAM STAIN

CROSS REFERENCE TO RELATED APPLICATIONS

This application is a continuation of International Application No. PCT/US2012/031454, filed Mar. 30, 2012; which claims priority to U.S. Provisional Appln. No. 61/470,661 filed Apr. 1, 2011, the entire contents of each of which are incorporated herein.

SEQUENCE LISTING

The instant application contains a Sequence Listing which has been submitted in ASCII format via EFS-Web and is hereby incorporated by reference in its entirety. Said ASCII copy, created on May 4, 2012, is named 119880-01202_SeqList.txt and 1,858 bytes in size.

FIELD OF THE INVENTION

The present invention relates to peptide nucleic acid (PNA) probes, PNA probe sets and methods for the analysis and sorting of microorganisms into Gram types. The invention further relates to diagnostic kits comprising such PNA probes.

BACKGROUND OF THE INVENTION

The Gram stain is universally used in microbiology as the initial step in identifying bacteria. It involves the use of crystal violet and iodine to stain fixed bacterial cells. Gram positive bacteria can be distinguished from Gram negative bacteria by their ability to retain the purple color of the crystal violet stain after washing with alcohol or acetone. Gram negative bacteria lose the purple color during the wash and are stained pink by the counter-stain, usually safranin or basic fuchsin, applied after the wash. Since Hans Christian Gram published his method for staining bacteria in 1884, demarcation of bacteria into so-called "Gram positive" and "Gram negative" types has become the first step in classifying and subdividing bacteria.

Since the Gram reactions are based on the physical properties of the cell wall they are inherently variable. Phenotypic properties such as presence of capsules and cell age as well as external factors such as growth conditions, and anti-bacterial agents affect the cell wall and can alter the staining qualities of the bacteria. The quality of a Gram stain can be affected by external factors as well. Gram staining is easily affected by technique—particularly the decolorization step (washing) of the assay. The percentage of acetone in the decolorizer, method of application, the thickness of the specimen, and the type of specimen can all effect the exposure time required for proper decolorization. If a preparation is over-decolorized, Gram types can be confused, also crystal violet precipitates can be mistaken for bacteria.

Not all bacteria are amenable to Gram staining. Some species are Gram-variable, taking on both Gram-positive and Gram-negative colorations. It is estimated that up to 10% of positive blood cultures yield Gram-variable bacteria. Other species react weakly with the Gram stain, making them Gram-indeterminate.

In the US, there are approximately 30 million blood cultures processed annually. The average positivity rate of these blood cultures is 10%, resulting in ~3 million positive blood cultures per year. It is a universal practice to test a positive blood culture to determine its Gram-stain result and thereby it's clinical/therapy implication for first line therapy choice. According to a recent study (Rand et al. *Am. J. Clin. Pathol.* 2006; 126:686-690), a retrospective, 23 month review of over 8,000 Gram stains revealed an error rate of ~0.7%. Extrapolation of this error rate nationwide would result in 21,000 Gram stain errors per year. Laboratories may also struggle with the differentiation of cocci in clusters vs. pairs and chains or for Gram-variable bacteria.

Improvements to the basic Gram stain technique have occurred. Automation of the Gram stain technique has been implemented to lower the variability from person to person and day to day. Alternate methods have been developed which effectively separate bacteria in to Gram types. Alternative dyes and methods have been developed to simplify the use of effective gram staining in specialized scenarios (Yazdankhah et al).

Sizemore et al describe a method employing fluorescein labeled wheat germ agglutinin to selectively label gram-negative bacteria. The method suffers the same downfalls of the original method in that it is susceptible to the inherent biological variability of the Gram stain target; namely the cell wall of the organisms and it lacks a way of positively identifying gram-positive organisms. Mason et al, and Holm and Jespersen made improvements to this method, and applied it to flow cytometric analysis.

U.S. Pat. Nos. 4,639,421 and 4,665,024 describe methods of differential staining of Gram types by application of two fluorescent dyes, in general a generic dye which is taken up by all organisms, and a second dye which is preferentially taken up by gram-negative organisms. The ratio of intensity of the dyes compared to a control is used to assign Gram-type.

Bidnenko et al describe a method of differentiating Gram types via differential penetration of high molecular weight peroxidase labeled DNA probes directed at cellular ribosomal RNA targets. Penetration of the peroxidase labeled probe into the cell indicate a Gram-negative organism since Gram-positives are impenetrable to high molecular weight molecules. Combined with a second probe of a different color which non-specifically labeled bacteria the presence of a fluorescent signature of the first label or coincidental detection of the first and second label, the organisms could be typed. This method uses the inherently variable cell well as a method to differentiate bacteria into Gram types, although the method overcame the lack of positive identification of gram-positive organisms which plagued the Sizemore method. It is important to point out that the Bidnenko method used a "universal" probe for detection of all bacteria. The method, again, relied on the different properties of the outer membrane of gram negative and gram positive organisms, not on the specificity of the probe to sort microorganisms into different gram types.

As is described in U.S. Patent Publication No. 2002/0081606, 2004/0171007, 2008/0118923 and elsewhere, several groups have used the polymerase chain reaction (PCR) as a way to amplify specific nucleic acid targets indicative of either Gram-positive or Gram-negative organisms (also see Carroll et al 2000, Klashick et al 2002). 16S rRNA (US2008/0118923), 23S rRNA (US 2004/0171007) or other genes such as sodA (US 2002/0081606) are used as amplification targets and Gram type is determined by signature of the amplicon. These methods although powerful are prone to the downfalls of amplified assays including false positives cause by target contamination, loss of distinction in mixed cultures, and destruction of the organism of interest, such that morphology information is not provided.

Hybridization assays directed at rRNA targets are frequently used to differentiate bacteria by species, genus, family, etc. Jansen, et al describe a method employing probe cocktails to detect virtually all potential organisms in a sample, and differentiating them into classes. The same basic method is used broadly. Roller et al describe a similar hybridization method to detect and differentiate most high G+C content gram-positive organisms. The authors suggest the method provides information relevant to monitoring sample populations in environments where obtaining classical staining information is unreliable.

The use of Gram stain to categorize bacteria has considerable problems related to the variability of the method from person to person, the inherently variable biological properties of the organisms, the subtleness and ability to accurately detect the indicating color change, and the presence of organisms which do not fit conveniently into either type (Gram variable or Gram intermediate).

Methods are needed which do not rely on the phenotypic characteristics such as membrane composition, have clear high contrast signals, use standard microbiological tools and techniques, and do not produce variable or indeterminate results.

SUMMARY OF THE INVENTION

Rapid methods for accurately establishing the classification of Gram-variable species would be valuable in the clinical microbiology laboratory to guide treatment decisions and to direct subsequent testing to determine the species identification.

An alternative to the Gram stain that produces definitive classification of all bacteria would likely also be a useful general tool for particular applications.

Kits of the invention are designed to detect rRNA sequences in a fashion which simulates the pattern of membrane staining in Gram stain. This approach allows for grouping of organisms into their "classic" Gram-types without actually requiring any knowledge of the composition of the membrane.

A preferred embodiment of the present invention features a molecular Gram stain which simulates the pattern of membrane staining in Gram stain. In one embodiment, the invention provides methods of grouping organisms into Gram types without the use of membrane stains.

The invention uses probes targeting ribosomal RNA rather than being dependent on the phenotypic qualities of the cell wall, and is not affected by changes in the cell wall. Accordingly, the present invention has certain advantages of molecular technologies (i.e. probes targeting ribosomal RNA) over conventional methods used for decades in clinical microbiology.

For Example, Exp. 3 shows examples of routine blood cultures yielding a non-conclusive variable Gram-stain results by traditional Gram-staining but yielding correct Gram-stain results using PNA probes of the present invention.

In certain preferred embodiments, the methods of the present invention may employ fluorescent labels to distinguish bacteria in high contrast from their surrounding milieu. Preferably, fluorescence makes the organisms easier to see and may increase sensitivity.

The PNA probes of the invention are particularly well-suited for fluorescence in situ hybridization (FISH) where the morphology of the cells is maintained to allow cell morphology to be assessed together with Gram-staining hereby mimicking the traditional Gram-stain method where often both Gram-stain and morphology is reported, i.e. Gram-negative rods or Gram-positive cocci in clusters.

The probes of the invention may be used in association with other probes, for instance probes which detect RNA targets in fungal cells, thereby producing a test which in multiplex can differentiate between Gram-positive, Gram-negative, and fungi as exemplified in Example 2, for example.

The probes of the invention may also be used in association with and/or in parallel to other probes, for instance probes for species identification, antibiotic susceptibility or other traits. This is exemplified in Example 4, for example, where Gram stain by PNA FISH is performed in parallel with PNA FISH for species identification on routine blood cultures. This allows Gram-stain and species identification to be provided by one procedure and results to be reported simultaneously. The latter solves a major drawback with current procedures where Gram-stain is reported followed later by species identification such that Gram-stain has higher impact on therapy decisions than species identification potentially leading to overuse of antibiotics, i.e. patients are started on antibiotic for multiple species based on Gram-stain results and once started often only changed to other therapy if therapy is not covering the particular species (whereas the incentive to change to more narrow therapy is often out-weighted by the risks and efforts associated with changing therapy).

Accordingly, in some embodiments, the present invention is directed to PNA probes and their use, as well as kits useful for the analysis of microorganisms optionally present in a sample of interest. In accordance with these embodiments, the PNA probes are directed to rRNA or the genomic sequences corresponding to said rRNA (rDNA) or its complement. In specific embodiments the probes of this invention are used for in situ hybridization analysis of microorganisms optionally present in a sample, most preferably the in situ hybridization analysis is fluorescence in situ hybridization analysis.

Accordingly, in certain embodiments PNA probes are provided for identifying microorganisms. As described herein, the term "identifying" or "identification" is meant to include either or both detection and quantitation.

In one aspect, the present invention features a PNA probe comprising CAC-CCT-CTC-AGG (Seq Id. No.1), or its complement, wherein at least a portion of the probe is at least about 75%, 80%, 81%, 82%, 83%, 84%, 85%, 86%, 87%, 88%, 89%, 90%, 91%, 92%, 93%, 94%, 95%, 96%, 97%, 98%, 99% identical to Seq Id. No.1.

In one embodiment, the invention features a PNA probe comprising CAC-CCT-CTC-AGG (Seq Id. No.1), or its complement, wherein at least a portion of the probe is at least about 83% identical to Seq Id. No.1.

In another embodiment, at least a portion of the probe is at least about 91% identical to Seq Id. No.1.

In another embodiment, the probe comprises Seq Id. No.1, or its complement.

In another embodiment, the probe consists of Seq Id. No.1, or its complement.

In another further embodiment, the probe is Seq Id. No.1.

In another particular embodiment, the probes of the present invention specifically recognize Gram positive organisms.

In another aspect, the present invention features a PNA probe specific for the detection, identification or quantification of Gram positive organisms comprising Seq Id. No. 1, or its complement, wherein the base at position 3 and/or the base at position 12 of Seq Id No.1 is unchanged.

Accordingly, in a related embodiment, the present invention features a PNA probe specific for the detection, identification or quantitation of Gram positive organisms, wherein the C at position 3 and/or the G at position 12 is unchanged, for example, but not limited to, Seq Id. No. 1.

In another aspect, the present invention features a PNA probe comprising TCC-TCT-CAG-ACC (Seq Id. No.2), or its complement, wherein at least a portion of the probe is at least about 75%, 80%, 81%, 82%, 83%, 84%, 85%, 86%, 87%, 88%, 89%, 90%, 91%, 92%, 93%, 94%, 95%, 96%, 97%, 98%, 99% identical to Seq Id. No.2.

In one embodiment, the invention features a PNA probe comprising TCC-TCT-CAG-ACC (Seq Id. No.2), or its complement, wherein at least a portion of the probe is at least about 83% identical to Seq Id. No.2.

In another embodiment, at least a portion of the probe is at least about 91% identical to Seq Id. No.2.

In another embodiment, the probe comprises Seq Id. No.2, or its complement.

In another embodiment, the probe consists of Seq Id. No.2, or its complement.

In another further embodiment, the probe is Seq Id. No.2.

In another embodiment, the probe specifically recognizes Gram negative organisms.

In another aspect, the present invention features a PNA probe specific for the detection, identification or quantification of Gram negative organisms comprising Seq Id. No. 2, or its complement, wherein the base at position 1 or the base at position 10 of Seq Id No. 2 is unchanged.

Accordingly, in a related embodiment, the present invention features a PNA probe specific for the detection, identification or quantitation of Gram negative organisms, wherein the T at position 1 and/or the A at position 10 is unchanged, for example, but not limited to, Seq Id. No. 2.

In another aspect, the present invention features a PNA probe comprising TCC-TCT-CDG-DCC (Seq Id. No.3), or its complement, wherein at least a portion of the probe is at least about 75%, 80%, 81%, 82%, 83%, 84%, 85%, 86%, 87%, 88%, 89%, 90%, 91%, 92%, 93%, 94%, 95%, 96%, 97%, 98%, 99% identical to Seq Id. No. 3.

In one preferred embodiment, the invention features a PNA probe comprising TCC-TCT-CDG-DCC (Seq Id. No.3), or its complement, wherein at least a portion of the probe is at least about 83% identical to Seq Id. No.3.

In another preferred embodiment, at least a portion of the probe is at least about 91% identical to Seq Id. No.3.

In another embodiment, the probe comprises Seq Id. No.3, or its complement.

In another embodiment, the probe consists of Seq Id. No.3, or its complement.

In another further embodiment, the probe is Seq Id. No.3.

In another embodiment, the probe specifically recognizes Gram negative organisms.

In another aspect, the present invention features a PNA probe specific for the detection, identification or quantification of Gram negative organisms comprising Seq Id. No. 3, or its complement, wherein the base at position 1, and/or the base at position 10 is unchanged.

In one embodiment, one or more bases at position 1 and position 10 of Seq Id No. 3 are unchanged.

Accordingly, in a related embodiment, the present invention features a PNA probe specific for the detection, identification or quantitation of Gram negative organisms, wherein the T at position 1 and/or the D at position 10 is unchanged, for example, but not limited to, Seq Id. No. 3.

In another aspect, the present invention features a PNA probe comprising CCC-TAG-TCG-GCA-TAG (Seq Id No.4), or its complement, wherein at least a portion of the probe is at least about 75%, 80%, 81%, 82%, 83%, 84%, 85%, 86%, 87%, 88%, 89%, 90%, 91%, 92%, 93%, 94%, 95%, 96%, 97%, 98%, 99% identical to Seq Id. No.4.

In one preferred embodiment, the invention features a PNA probe comprising CCC-TAG-TCG-GCA-TAG (Seq. Id No. 4), or its complement, wherein at least a portion of the probe is at least about 83% identical to Seq Id. No.4.

In another preferred embodiment, at least a portion of the probe is at least about 91% identical to Seq Id. No.4.

In another embodiment, the probe comprises Seq Id. No.4, or its complement. In another embodiment, the probe consists of Seq Id. No.4, or its complement.

In another further embodiment, the probe is Seq Id. No 4.

In another aspect, the present invention features a PNA probe comprising CCA-AGA-GAT-CCG-TTG (Seq. Id No. 5), or its complement, wherein at least a portion of the probe is at least about 75%, 80%, 81%, 82%, 83%, 84%, 85%, 86%, 87%, 88%, 89%, 90%, 91%, 92%, 93%, 94%, 95%, 96%, 97%, 98%, 99% identical to Seq Id. No.5.

In one preferred embodiment, the invention features a PNA probe comprising CCA-AGA-GAT-CCG-TTG (Seq. Id No. 5), or its complement, wherein at least a portion of the probe is at least about 83% identical to Seq Id. No.5.

In another preferred embodiment, at least a portion of the probe is at least about 91% identical to Seq Id. No.5.

In another embodiment, the probe comprises Seq Id. No.5, or its complement.

In another embodiment, the probe consists of Seq Id. No.5, or its complement.

In another further embodiment, the probe is Seq Id. No.5.

In one embodiment, the probes of the present invention (i.e. Seq Id Nos 1, 2, 3, 4 or 5) contain less than 20, 19, 18, 17, 16, 15, 14, 13, 12, 11, 10, 9 or 8 nucleobases. In certain preferred embodiments, the probes of the present invention are preferably between 8-17, 8-16, 8-15, 8-14, 8-13, 8-12, 9-17, 9-16, 9-15, 9-14, 9-13, 9-12, 10-17, 11-17, 10-17, 10-16, 10-15, 10-14, 10-13, 10-12, 10-11, 11-17, 11-16, 11-15, 11-14, 11-13, 11-12 nucleobases.

In further preferred embodiments, the probes are 11-13 nucleobases and in other further embodiments are most preferably 12 nucleobases in length.

These PNA probes have the inherent physico/chemical characteristics of PNA probes as compared to nucleic acid probes, such that rapid and accurate analysis can be performed using just a single PNA probe. Furthermore, many microorganisms have a relatively rigid cell wall where the improved penetration of PNA probes also offers an advantage as compared to nucleic acid probes when applied in fluorescence in situ hybridization assays. Where nucleic acid probes require fixation and permeabilization with cross-linking agents and/or enzymes (for example see Kempf et al., *J. Clin. Microbiol* 38:830-838 (2000)), these PNA probes can be applied directly following smear preparation as exemplified in example 1.

In a preferred embodiment, these PNA probes have a relatively short nucleobase sequence, such as 8-17 bases. In preferred embodiments, the PNA probes are 12 nucleobases. In other preferred embodiments, they are 15 nucelobases as described in example 1. Naturally occurring nucleic acid probes are typically at least 18 nucleobases (For example see Kempf et al., *J. Clin. Microbiol* 38:830-838 (2000)) due to their lower Tm values. This difference provides these PNA probes with better discrimination to closely related non-target sequences with only a single or just a few nucleobase difference(s) as required for analysis of rRNA or rDNA from microorganisms.

PNA probe nucleobase sequences according to the invention are selected from the group consisting of: CAC-CCT-CTC-AGG (Seq Id. No.1), and TCC-TCT-CAG-ACC (Seq Id. No.2). One or more of these probes, or the complements thereof, are included in the most preferred probe sets of this invention.

In a preferred embodiment of this invention, one or more probes may contain nucleoside analogs. In further preferred embodiments, the nucleoside analog is preferably 2' diaminopurine used in place of adenine.

In a preferred embodiment, Seq Id No 2 contains two 2,6-diaminopurine bases (denoted as "D") at positions 8 and 10 in the sequence such that it reads TCC-TCT-CDG-DCC. (Seq Id No 3).

Preferably probes of this invention are labeled with at least one detectable moiety, wherein the detectable moiety or moieties are selected from the group consisting of:
a conjugate, a branched detection system, a chromophore, a fluorophore, a spin label, a radioisotope, an enzyme, a hapten, an acridinium ester and a luminescent compound. Fluorescent labeled probes of this invention may be self-reporting, preferably self-reporting fluorescent probes of this invention are PNA Linear Beacons, most preferably self-reporting fluorescent probes of this invention are PNA Probe-Quencher pairs.

The present invention provides peptide nucleic acids (PNAs), that bind complementary ssDNA and RNA strands. The compounds of the invention generally comprise ligands linked to a peptide backbone. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, etc.) attached to a peptide backbone through a suitable linker. WO 92/20702 describes PNAs wherein such ligands are linked to a polyamide backbone solely through aza nitrogen atoms. T In certain preferred embodiments, the peptide nucleic acids of the invention have the general formula (I):

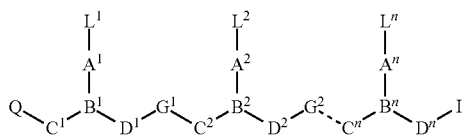

wherein:
n is at least 2,
each of $L^1$-$L^n$ is independently selected from the group consisting of hydrogen, hydroxy, ($C_1$-$C_4$)alkanoyl, naturally occurring nucleobases, non-naturally occurring nucleobases, aromatic moieties, DNA intercalators, nucleobase-binding groups, heterocyclic moieties, and reporter ligands, at least one of $L^1$-$L^n$ being a naturally occurring nucleobase, a non-naturally occurring nucleobase, a DNA intercalator, or a nucleobase-binding group;
each of $C^1$-$C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, ($C_2$-$C_6$)alkyl, aryl, aralkyl, heteroaryl, hydroxy, ($C_1$-$C_6$)alkoxy, ($C_1$-$C_6$)alkylthio, $NR^3R^4$ and $SR^5$, where $R^3$ and $R^4$ are as defined above, and $R^5$ is hydrogen, ($C_1$-$C_6$)alkyl, hydroxy-, alkoxy-, or alkylthio-substituted ($C_1$-$C_6$)alkyl, or $R^6$ and $R^7$ taken together complete an alicyclic or heterocyclic system;
each of $D^1$-$D^n$ is $(CR^6R^7)_z$ where $R^6$ and $R'^7$ are as defined above;
each of y and z is zero or an integer from 1 to 10, the sum y+z being greater than 2 but not more than 10;
each of $G^1$-$G^{n-1}$ is —$NR^3CO$—, —$NR^3CS$—, —$NR^3SO$— or —$NR^3SO_2$—, in either orientation, where $R^3$ is as defined above;
each pair of $A^{1-A\ n}$ and $B1$-$B\ n$ are selected such that:
(a) A is a group of formula (IIa), (IIb) or (IIc) and B is N or $R^{3N.+}$; or
(b) A is a group of formula (IId) and B is CH;

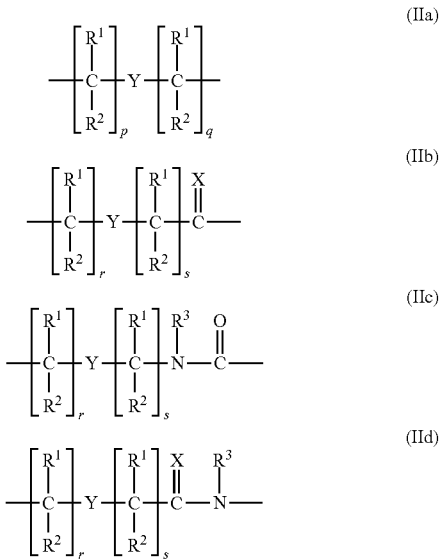

where
X is O, S, Se, $NR^3$, $CH_2$ or $C(CH_3)_2$;
Y is a single bond, O, S or $NR^4$;
each of p and q is zero or an integer from 1 to 5, the sum p+q being not more than 10;
each of r and s is zero or an integer from 1 to 5, the sum r+s being not more than 10;
each $R^1$ and $R^2$ is independently selected from the group consisting of hydrogen, ($C_1$-$C_4$)alkyl which may be hydroxy- or alkoxy- or alkylthio-substituted, hydroxy, alkoxy, alkylthio, amino and halogen;
each of $G.^1$-$G^{n-1}$ is —$NR^3CO$—. —$NR^3CS$—, —$NR^3SO$— or —$NR^3SO_2$, in either orientation, where $R^3$ is as defined above;
Q is —$CO_2H$, —$CONR'R"$, —$SO_3H$ or —$SO_2N'RR"$ or an activated derivative of —$CO_2H$ or —$SO_3H$; and
I is —$NHR'''R''''$ or —$NR'''C(O)R''''$, where R', R", R''' and R'''' are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers.

In certain embodiments, at least one A is a group of formula (IIc) and B is N or $R^3N$. In other embodiments, A is a group of formula (IIa) or (IIb), B is N or R.sup.3 N.sup.+, and at least one of y or z is not 1 or 2.

In certain embodiments, peptide nucleic acids have general formula (IIIa) or (IIIb): wherein:

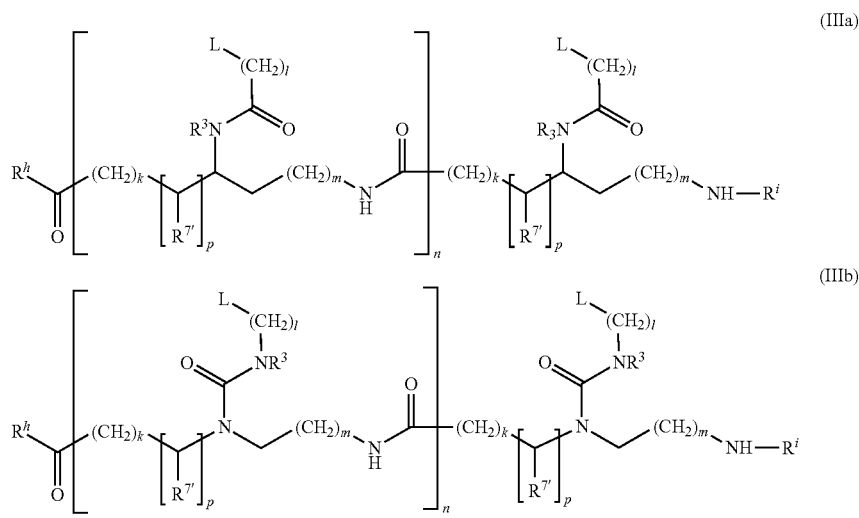

each L is independently selected from the group consisting of hydrogen, phenyl, heterocyclic moieties, naturally occurring nucleobases, and non-naturally occurring nucleobases; each $R^{7'}$ is independently selected from the group consisting of hydrogen and the side chains of naturally occurring alpha amino acids;

n is an integer from 1 to 60;

each of k, l, and m is independently zero or an integer from 1 to 5;

p is zero or 1;

$R^h$ is OH, $NH_2$ or $-NHLysNH_2$; and $R^i$ is H or $COCH_3$.

Particularly preferred are compounds having formula (IIIa) or (IIIb) wherein each L is independently selected from the group consisting of the nucleobases thymine (T), adenine (A), cytosine (C), guanine (G) and uracil (U), k and m are zero or 1, and n is an integer from 1 to 30, in particular from 4 to 20.

Synthesis of the PNAs of the invention is by adaptation of standard peptide synthesis procedures, either in solution or on a solid phase. Synthesis is described, for example, in U.S. Pat. No. 5,539,082.

Methods for the chemical assembly of PNAs are known (See for example: U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470). As a general reference for PNA synthesis methodology please see: Nielsen et al., Peptide Nucleic Acids; Protocols and Applications, Horizon Scientific Press, Norfolk England (1999).

In certain preferred embodiments of the present invention, modifications can be made to the pseudopeptide backbone of the probe. Such modifications may introduce advantageous properties to the probe for instance by introducing handedness/chirality to the probe, or by introducing internal sites for the addition of solubility enhancers or labels, or both. An example of a modification to the pseudopeptide backbone is the so called Gamma substitutions exemplified in Englund and Appella (*Org. Letters*, 2005, incorporated by reference in its entirety herein). Preferably, such modifications are made at position K in Formula 1 above.

In other embodiments of the present invention PNA probes are included which contain moieties that add functionality to the probe. Such moieties include but are not limited to spacer and linker groups. Likewise, PNA probes of this invention encompass probes attached to a solid support such as but not limited to a membrane, a slide, an array, a bead, or a particle.

Probe sets of this invention include two or more PNA probes for the analysis of microorganisms optionally present in a sample. Probe sets are preferably labeled with a detectable moiety. Probe sets may be labeled with the same detectable moiety, or they may be differently labeled for independent analysis of probe signals. It is within the conception of this invention that two or more differently labeled fluorescent probes of a probe set may be used to create a third signal by coincidental fluorescence.

By "detectable moiety" is intended to include any compound, label, or moiety that absorbs energy, typically from an illumination source, to reach an electronically excited state, and then emits energy, typically at a characteristic wavelength, to achieve a lower energy state. For example but without limitation, when certain fluorophores are illuminated by an energy source with an appropriate excitation wavelength, typically an incandescent or laser light source, photons in the fluorophore are emitted at a characteristic fluorescent emission wavelength. Fluorophores, sometimes referred to as fluorescent dyes, may typically be divided into families, such as fluorescein and its derivatives; rhodamine and its derivatives; cyanine and its derivatives; coumarin and its derivatives; Cascade Blue™ and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa Fluor 488, Alexa Fluor 532, Alexa Fluor 546, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine™), carboxy tetramethylrhodamine (TAMRA™), carboxy-X-rhodamine (ROX™), LIZ™, VIC™, NED™, PET™, SYBR, PicoGreen, RiboGreen, and the like. Descriptions of fluorophores and their use, can be found in, among other places, R. Haugland, *Handbook of Fluorescent Probes and Research Products*, 9.sup.th ed. (2002), Molecular Probes, Eugene, Oreg.; M. Schena, *Microarray Analysis* (2003), John Wiley & Sons, Hoboken, N.J.; *Synthetic Medicinal Chemistry* 2003/2004 Catalog, Berry and Associates, Ann Arbor, Mich.; G. Hermanson, *Bioconjugate Techniques*, Academic Press (1996); and *Glen Research* 2002 *Catalog*, Sterling, Va. Near-infrared dyes are expressly within the intended meaning of the terms fluorophore and fluorescent reporter group.

In certain embodiments, the present invention features methods for the identification (i.e. detection, identification or quantitation) of microorganisms in a biological sample, said method comprising contacting the sample with one or more PNA probes as described herein; and detecting hybridization of the one or more PNA probes to one or more rRNA molecules in the sample, wherein detection of rRNA is indicative of the presence, identity or amount of microorganisms in the sample.

The present invention is the first time that Gram-staining has been carried out using PNA probes.

According to further related embodiments, the presence, absence and/or number of microorganisms in the sample are detected, identified and/or quantitated and/or the susceptibility to antibiotics is determined by correlating the hybridization, under suitable hybridization conditions, of the probing nucleobase sequence of the probe to the target sequence. Consequently, the analysis is based on a single assay with a definitive outcome. In contrast, current routine methods for analysis of microorganisms are based on multiple phenotypic characteristics involving multiple tests.

In exemplary embodiments, the methods of this invention are used for in situ hybridization analysis of microorganisms optionally present in a sample, most preferably the in situ hybridization analysis is fluorescence in situ hybridization analysis. In preferred methods of the invention, the sample is a biological sample, including but not limited to blood, urine, secretion, sweat, bronchoalveolar lavage, sputum, stool, mucous, or cultures thereof.

Methods of the invention optionally include non-labeled blocking probes to reduce or eliminate hybridization of PNA probes to non-target sequences. Methods of this invention do not include the use of cross-linking reagents or enzymes prior to hybridization.

In certain preferred embodiments, the method may include contacting the sample with another probe for signal amplification or detection of one or more other species.

The methods of this invention may also be used to detect nucleic acid targets generated, synthesized or amplified in a reaction. Preferred methods for generating, synthesizing or amplifying targets include PCR, LCR, SDA, TMA, RCA and Q-beta replicase.

Methods of the invention include those in which the targets are immobilized to a surface, such as a membrane, a slide, a bead, or a particle and which may furthermore be a component of an array. Optionally, the methods may include PNA probes which are immobilized to a surface such as a membrane, a slide, a bead, or a particle, and may furthermore be a component of an array.

In certain preferred embodiments, the present invention includes methods of treating a subject suffering from an infection comprising a) obtaining a biological sample from the subject; b) identifying one or more microorganisms in the sample according to any one of the aspects or embodiments described herein; and c) administering at least one antibiotic with activity towards the one or more microorganisms, thereby treating the infection.

In still another embodiment, this invention is directed to kits suitable for performing an assay that detect, identify and/or quantitate microorganisms optionally present in a sample and/or determination of antibiotic resistance. The kits of this invention comprise one or more PNA probes and other reagents or compositions that are selected to perform an assay or otherwise simplify the performance of an assay. Preferred kit formats include kits designed to perform in situ hybridization assays, and kits designed to perform real-time PCR assays. Preferred kits are designed to examine samples such as clinical specimens, or cultures thereof.

Those of ordinary skill in the art will appreciate that a suitable PNA probe need not have exactly these probing nucleobase sequences to be operative but often modified according to the particular assay conditions. For example, shorter PNA probes can be prepared by truncation of the nucleobase sequence if the stability of the hybrid needs to be modified to thereby lower the Tm and/or adjust for stringency. Similarly, the nucleobase sequence may be truncated at one end and extended at the other end as long as the discriminating nucleobases remain within the sequence of the PNA probe. Such variations of the probing nucleobase sequences within the parameters described herein are considered to be embodiments of this invention.

The PNA probes, methods and kits of this invention have been demonstrated to be both sensitive and specific for the microorganisms they are direct to. Moreover, the assays described herein are rapid (less than 3 hours) and capable of analysis of microorganisms in a single assay.

Those of ordinary skill in the art will also appreciate that the complement probing sequence is equally suitable for assays, such as but not limited to real-time PCR, that are using rDNA as target.

BRIEF DESCRIPTION OF THE DRAWINGS

Various embodiments of the present disclosure will be described herein below with reference to the figures wherein:

FIG. 1: Process for Determining Species Specific PNA FISH Slide Selection

DETAILED DESCRIPTION OF THE INVENTION

I. Definitions

As used herein, the term "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids.

As used herein, the term "nucleobase sequence" means any segment of a polymer that comprises nucleobase-containing subunits. Non-limiting examples of suitable polymers or polymer segments include oligodeoxynucleotides, oligoribonucleotides, peptide nucleic acids, nucleic acid analogs, nucleic acid mimics, and/or chimeras.

As used herein, the term "target sequence" means the nucleobase sequence that is to be detected in an assay.

As used herein, the term "probe" means a polymer (e.g. a DNA, RNA, PNA, chimera or linked polymer) having a probing nucleobase sequence that is designed to sequence-specifically hybridize to a target sequence of a target molecule of an organism of interest.

As used herein, the term "analyze" means that the individual bacteria are marked for detection, identification and/or quantitation and/or for determination of resistance to antibiotics (antimicrobial susceptibility).

As used herein, the term "identification" is meant to refer to the establishment of the identity of the organism by taxon, for example, genus and/or species name. The term "identification" or "identifying" is meant to include either or both detection and quantitation.

As used herein, the term "detection" is meant to refer to analysis for the presence or absence of the organism optionally present in the sample.

As used herein, the term "quantitation" is meant to refer to enumeration of the organisms in a sample.

As used herein, the term "peptide nucleic acid" or "PNA" means any oligomer, linked polymer or chimeric oligomer, comprising two or more PNA subunits (residues), including any of the polymers referred to or claimed as peptide nucleic acids in U.S. Pat. Nos. 5,539,082, 5,527,675, 5,623,049, 5,714,331, 5,736,336, 5,773,571, 5,786,461, 5,837,459, 5,891,625, 5,972,610, 5,986,053, 6,107,470 and 6,357,163. In the most preferred embodiment, a PNA subunit consists of a naturally occurring or non-naturally occurring nucleobase attached to the aza nitrogen of the N-[2-(aminoethyl)] glycine backbone through a methylene carbonyl linkage.

As used herein, the terms "label" and "detectable moiety" are interchangeable and shall refer to moieties that can be attached to a probe to thereby render the probe detectable by an instrument or method.

As used herein, "discriminating base" or "discriminating bases" is meant to refer to one or more nucleobases that are necessary for the detection, identification and/or quantitation of Gram positive organisms. In certain embodiments, the term "discriminating base" refers to one or more bases of Seq Id No. 1 or Seq Id No. 2 or Seq Id No. 3 or Seq Id No. 4 or Seq Id No. 5 that are necessary for the detection, identification and/or quantitation of microorganisms, i.e. bases at position 3 and/or 12 of Seq. Id. No. 1 and bases at position 1 and/or 10 of Seq. Id. No. 2 and 3.

The term "Gram-negative bacteria" is meant to refer to a group of bacteria which, during the Gram-stain method, do not retain crystal violet, and are stained pink. Exemplary gram negative bacteria include, but are not limited to, *Enterobacter, Escherichia coli, Pseudomonas, Klebsiella, Acinetobacter, Raoultella, Salmonella, Serratia, Shigella, Stenotrophomonas, Vibrio* and *Haemophilus*. Other exemplary gram negative bacteria include, but are not limited to, *Moraxella catarrhalis, Acinetobacter baumannii, Acinetobacter calcoaceticus, Acinetobacter haemolyticus, Acinetobacter junii, Acinetobacter radioresistens, Aeromonas hydrophila, Cardiobacterium hominis, Eikenella corrodens, Enterobacter aerogenes, Enterobacter cloacae, Haemophilus influenza, Klebsiella oxytoca, Klebsiella pneumoniae, Providencia stuartii, Pseudomonas aeruginosa, Pseudomonas fluorescens, Pseudomonas putida, Pseudomonas stutzeri, Raoultella terrigena, Raoutella planticola, Salmonella enterica* subsp *enterica, Serratia marcescens, Shigella boydii, Stenotrophomonas maltophilia, Stenotrophomonas maltophilia*, and *Vibrio vulnificus*.

As used herein, the term "gram positive bacteria" is meant to refer to any bacteria that is stained dark blue or violet by Gram staining. Exemplary gram positive bacteria include, but are not limited to, *Bacillus, Enterococcus, Staphylococcus*, and *Streptococcus*. Other exemplary gram positive bacteria include, but are not limited to, *Bacillus cereus, Bacillus sphaericus, Corynebacterium renale, Enterococcus casseliflavus, Enterococcus columbae, Enterococcus durans, Enterococcus faecalis, Enterococcus faecium, Enterococcus hirae, Enterococcus malodoratus, Enterococcus raffinosus, Enterococcus saccharolyticus, Staphylococcus aureus, Staphylococcus capitis, Staphylococcus epidermidis, Staphylococcus gallinarum, Staphylococcus lugdunensis, Staphylococcus schleiferi* subsp *schleiferi, Staphylococcus sciuri* subsp. *Sciuri, Staphylococcus simulans, Staphylococcus warneri, Staphylococcus xylosus, Streptococcus intermedius, Streptococcus agalactiae, Streptococcus bovis, Streptococcus iniae, Streptococcus oralis, Streptococcus phocae, Streptococcus pyogenes, Streptococcus thoraltensis, Streptococcus uberis*.

The phrase "at least about 83% identical" with respect to two sets of nucleic acid sequences refers to the percentage of residues that are identical in the two sequences when the sequences are optimally aligned. Thus, at least 83% identical means that at least 83% of nucleobases in two or more optimally aligned PNA probe sequences are identical. In certain aspects, the present invention features a PNA probe comprising TCC-TCT-CAG-ACC (Seq Id. No.2), or its complement, wherein at least a portion of the probe is at least about 75%, 80%, 81%, 82%, 83%, 84%, 85%, 86%, 87%, 88%, 89%, 90%, 91%, 92%, 93%, 94%, 95%, 96%, 97%, 98%, 99% identical to Seq Id. No.2.

The term "coincidental fluorescence" as used herein is used to describe the perception of a color which is generated by the simultaneous detection of light emissions of two or more labels located near enough in space so as to be irresolvable. The detection of coincidental fluorescence can be either by eye or a photon-sensitive device.

The term "biological sample" is meant to refer to any sample from a human subject, e.g. cells, tissues, blood, or other fluids. In preferred embodiments, the biological sample is selected from simulated blood cultures, hospital blood cultures (sub-aliquots of actual blood cultures from human patients) and bronchial alveolar lavage (BAL) samples (sub-aliquots of actual BALs from human patients)

2. Description

I. General:

PNA Synthesis:

Methods for the chemical assembly of PNAs are well known (see: U.S. Pat. Nos. 5,539,082, 5,527,675, 5,623,049, 5,714,331, 5,736,336, 5,773,571, 5,786,461, 5,837,459, 5,891,625, 5,972,610, 5,986,053 and 6,107,470).

PNA Labeling:

Preferred non-limiting methods for labeling PNAs are described in U.S. Pat. Nos. 6,110,676, 6,361,942, 6,355,421, the examples section of this specification or are otherwise well known in the art of PNA synthesis and peptide synthesis.

Labels:

Non-limiting examples of detectable moieties (labels) suitable for labeling PNA probes used in the practice of this invention would include a dextran conjugate, a branched nucleic acid detection system, a chromophore, a fluorophore, a spin label, a radioisotope, an enzyme, a hapten, an acridinium ester and a chemiluminescent compound.

Other suitable labeling reagents and preferred methods of attachment would be recognized by those of ordinary skill in the art of PNA, peptide or nucleic acid synthesis.

Preferred haptens include 5 (6)-carboxyfluorescein, 2,4-dinitrophenyl, digoxigenin, and biotin.

Preferred fluorochromes (fluorophores) include 5 (6)-carboxyfluorescein (Flu), 6-((7-amino-4-methylcoumarin-3-acetyl)amino) hexanoic acid (Cou), 5 (and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.), JOE, Tamara or the Alexa dye series (Molecular Probes, Eugene, Oreg.).

Preferred enzymes include polymerases (e.g. Taq polymerase, Klenow PNA polymerase, T7 DNA polymerase, Sequenase, DNA polymerase 1 and phi29 polymerase), alkaline phosphatase (AP), horseradish peroxidase (HRP) and most preferably, soy bean peroxidase (SBP).

Unlabeled Probes:

The probes that are used for the practice of this invention need not be labeled with a detectable moiety to be operable within the methods of this invention, for example when attached to a solid support Self-Indicating Probes:

Beacon probes are examples of self-indicating probes which include a donor moiety and a acceptor moiety. The donor and acceptor moieties operate such that the acceptor moieties accept energy transferred from the donor moieties or otherwise quench signal from the donor moiety. Though the previously listed fluorophores (with suitable spectral properties) might also operate as energy transfer acceptors, preferably, the acceptor moiety is a quencher moiety. Preferably, the quencher moiety is a non-fluorescent aromatic or heteroaromatic moiety. The preferred quencher moiety is 4-((-4-(dimethylamino) phenyl) azo)benzoic acid (dabcyl). In a preferred embodiment, the self-indicating Beacon probe is a PNA Linear Beacon as more fully described in U.S. Pat. No. 6,485,901.

In another embodiment, the self-indicating probes of this invention are of the type described in WIPO patent application WO97/45539, incorporated by reference in its entirety herein. These self-indicating probes differ as compared with Beacon probes primarily in that the reporter must interact with the nucleic acid to produce signal.

Another example is exemplified in US 20100196887 incorporated by reference in its entirety herein.

Another example is exemplified in Fiandaca et al., Self-reporting PNA/DNA primers for PCR analysis. Genome Res. 2001 April; 11(4):609-13. incorporated by reference in its entirety herein.

Spacer/Linker Moieties:

Generally, spacers are used to minimize the adverse effects that bulky labeling reagents might have on hybridization properties of probes. Preferred spacer/linker moieties for the nucleobase polymers of this invention consist of one or more aminoalkyl carboxylic acids (e.g. aminocaproic acid), the side chain of an amino acid (e.g. the side chain of lysine or omithine), natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane).

Hybridization Conditions/Stringency:

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target sequence combination is often found by the well known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay may be experimentally determined by examination of each stringency factor until the desired degree of discrimination is achieved.

Suitable Hybridization Conditions:

Generally, the more closely related the background causing nucleic acid sequences are to the target sequence, the more carefully stringency must be controlled. Blocking probes may also be used as a means to improve discrimination beyond the limits possible by optimization of stringency factors. Suitable hybridization conditions will thus comprise conditions under which the desired degree of discrimination is achieved such that an assay generates an accurate (within the tolerance desired for the assay) and reproducible result.

Aided by no more than routine experimentation and the disclosure provided herein, those of skill in the art will easily be able to determine suitable hybridization conditions for performing assays utilizing the methods and compositions described herein. Suitable in-situ hybridization or PCR conditions comprise conditions suitable for performing an in-situ hybridization or PCR procedure. Thus, suitable in-situ hybridization or PCR conditions will become apparent to those of skill in the art using the disclosure provided herein, with or without additional routine experimentation.

Blocking Probes:

Blocking probes are nucleic acid or non-nucleic acid probes that can be used to suppress the binding of the probing nucleobase sequence of the probing polymer to a non-target sequence. Preferred blocking probes are PNA probes (see: U.S. Pat. No. 6,110,676). It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocking probes can be used with the methods, kits and compositions of this invention to suppress the binding of the probes to a non-target sequence that might be present and interfere with the performance of the assay. Blocking probes are particularly advantageous for discrimination to the phylogenetically closest related species.

Probing Nucleobase Sequence:

A probing nucleobase sequence can be designed to hybridize with a PNA probe sequence encompassed by any of the above sequences, (i.e. Seq Id. No. 1, Seq Id. No. 2, Seq Id. No. 3, Seq Id. No. 4 or Seq Id. No. 5), and particularly those portions specified above.

Probing nucleobase sequences used according to certain preferred aspects of the present invention are those having a length selected from a range of about 10 to about 25 bases preferably about 10 to about 20 bases, more preferably about 11 to about 15 bases, most preferably about 11 to about 13 bases. Preferably, the probing nucleobase sequences of the present invention features at least 20, at least 19, at least 18, at least 17, at least 16, at least 15, at least 14, at least 13, at least 12, at least 11, at least 10, at least 9, at least 8, at least 7, at least 6, at least 5, at least 4, at least 3, or at least 2 bases that hybridizes to a specific target sequence.

According to preferred embodiments of the present invention, the probing nucleobase sequence of a probe of this invention is the specific sequence recognition portion of the construct. Therefore, the probing nucleobase sequence is a nucleobase sequence designed to hybridize to a specific target sequence wherein the presence, absence or amount of the target sequence can be used to directly or indirectly detect the presence, absence or number of organisms of interest in a sample. Consequently, with due consideration to the requirements of a probe for the assay format chosen, the length and sequence composition of the probing nucleobase sequence of the probe will generally be chosen such that a stable complex is formed with the target sequence under suitable hybridization conditions.

In one embodiment, the preferred probing nucleobase sequence of the probe of this invention that is suitable for the detection, identification and/or quatitation of Gram positive organisms comprises a nucleobase sequence of: CAC-CCT-CTC-AGG (Seq. Id No. 1) and the complement thereto.

In another embodiment, the preferred probing nucleobase sequence of the probe of this invention that is suitable for the detection, identification and/or quantitation of Gram negative organisms comprises a nucleobase sequence of: TCC-TCT-CAG-ACC (Seq. Id No. 2) and the complement thereto.

In another embodiment, the preferred probing nucleobase sequence of the probe of this invention that is suitable for the detection, identification and/or quantitation of Gram negative organisms comprises a nucleobase sequence of: TCC-TCT-CDG-DCC (Seq. Id No. 3) and the complement thereto.

In another further embodiment, the preferred probing nucleobase sequence of the probe of this invention that is suitable for the detection, identification and/or quantitation of fungal organisms comprises a nucleobase sequence of: CCC-TAG-TCG-GCA-TAG (Seq. Id No. 4) and the complement thereto.

In another further embodiment, the preferred probing nucleobase sequence of the probe of this invention that is suitable for the detection, identification and/or quantitation of fungal organisms comprises a nucleobase sequence of: CCA-AGA-GAT-CCG-TTG (Seq. Id No. 5) and the complement thereto.

This invention contemplates that variations in these identified probing nucleobase sequences shall also provide probes that are suitable for the analysis of microorganisms. Variations of the probing nucleobase sequences within the parameters described herein are considered to be an embodiment of this invention.

For example, a variation can be a deletion, insertion or addition, or a substitution. A "deletion" is meant to refer a change in a nucleotide sequence in which one or more nucleotide residues are absent as compared to the naturally occurring sequence.

An "insertion" or "addition" is meant to refer to a change in a nucleotide sequence which has resulted in the addition of one or more nucleotide residues, as compared to the naturally occurring sequence.

A "substitution" is meant to refer to a replacement of one or more nucleotides by different nucleotides, as compared to the naturally occurring sequence.

According to preferred embodiments of the invention, the present inventors have identified certain "discriminating bases" that are necessary for the detection, identification and/or quantitation of Gram positive organisms.

In certain preferred embodiments of the present invention, at least one discriminating base of Seq Id No. 1 is required for the detection, identification and/or quantitation of Gram positive organisms. In another related embodiment, at least two discriminating bases of Seq Id No. 1 are required for the detection, identification and/or quantitation of Gram positive organisms. According to further related embodiments, the key discriminating bases of Seq Id. No. 1 are shown below as underlined.

(Seq. Id No. 1)
CA<u>C</u>-CCT-CTC-AG<u>G</u>

Accordingly, the present invention features PNA probes specific for the detection, identification or quantification of Gram positive organisms comprising Seq Id. No. 1, or its complement, wherein the base at position 3 and/or the base at position 12 of Seq Id No. 1 is unchanged.

In certain exemplary embodiments, the present invention features a PNA probe specific for the detection, identification or quantitation of Gram positive organisms, wherein the C at position 3 and/or the G at position 12 is unchanged, for example, but not limited to, Seq Id. No. 1. That is, the probe can be any length, or comprise one or more modifications, but in order to be specific for the detection, identification or quantification of Gram positive organisms, as set forth in the present invention, the probing sequence must include a C at position 3 and/or a G at position 12.

According to preferred embodiments of the invention, the present inventors have identified certain "discriminating bases" that are necessary for the detection, identification and/or quantitation of Gram negative organisms. In certain preferred embodiments of the present invention, at least one discriminating base of Seq Id No. 2 is required for the detection, identification and/or quantitation of Gram negative organisms. In another related embodiment, at least two discriminating bases of Seq Id No. 2 are required for the detection, identification and/or quantitation of Gram negative organisms. According to further related embodiments, the key discriminating bases of Seq Id. No. 2 are shown below as underlined.

(Seq. Id No. 2)
<u>T</u>CC-TCT-CAG-<u>A</u>CC

Accordingly, the present invention features PNA probes specific for the detection, identification or quantification of Gram negative organisms comprising Seq Id. No. 2, or its complement, wherein the base at position 1 and/or the base at position 10 of Seq Id No.2 is unchanged.

In certain exemplary embodiments, the present invention features a PNA probe specific for the detection, identification or quantitation of Gram negative organisms, wherein the T at position 1 and/or the A at position 10 is unchanged, for example, but not limited to, Seq Id. No. 2. That is, the probe can be any length, or comprise one or more modifications, but in order to be specific for the detection, identification or quantification of Gram negative organisms, as set forth in the present invention, the probing sequence must include a T at position 1 and/or a A at position 10.

According to preferred embodiments of the invention, the present inventors have identified certain "discriminating bases" that are necessary for the detection, identification and/or quantitation of Gram negative organisms. In certain preferred embodiments of the present invention, at least one discriminating base of Seq Id No. 3 is required for the detection, identification and/or quantitation of Gram negative organisms. In another related embodiment, at least two discriminating bases of Seq Id No. 3 are required for the detection, identification and/or quantitation of Gram negative organisms. According to further related embodiments, the key discriminating bases of Seq Id. No. 3 are shown below as underlined.

(Seq. Id No. 3)
<u>T</u>CC-TCT-CDG-<u>D</u>CC

Accordingly, the present invention features PNA probes specific for the detection, identification or quantification of Gram negative organisms comprising Seq Id. No. 3, or its complement, wherein the base at position 1 and/or the base at position 10 of Seq Id No.3 is unchanged.

In certain exemplary embodiments, the present invention features a PNA probe specific for the detection, identification or quantitation of Gram negative organisms, wherein the T at position 1 and/or the D at position 10 is unchanged, for example, but not limited to, Seq Id. No. 3. That is, the probe can be any length, or comprise one or more modifications, but in order to be specific for the detection, identification or quantification of Gram negative organisms, as set forth in the present invention, the probing sequence must include a T at position 1 and/or a D at position 10.

Variations may occur in one of the bases that are not identified as "discriminating bases" as described herein. Common variations include, but are not necessarily limited to, deletions, insertions and frame shifts. Additionally, a shorter probing nucleobase sequence can be generated by truncation of the sequence identified above.

A probe of this invention will generally have a probing nucleobase sequence that is exactly complementary to the target sequence. Alternatively, a substantially complementary probing nucleobase sequence might be used since it has been demonstrated that greater sequence discrimination can be obtained when utilizing probes wherein there exists one or more point mutations (base mismatch) between the probe and the target sequence (See: Guo et al., *Nature Biotechnology* 15: 331-335 (1997)). Consequently, the probing nucleobase sequence may be only 90% homologous to the probing nucleobase sequences identified above. Substantially complementary probing nucleobase sequence within the parameters described above are considered to be an embodiment of this invention. Complements of the probing nucleobase sequence are considered to be an embodiment of this invention, since it is possible to generate a suitable probe if the target sequence to be detected has been amplified or copied to thereby generate the complement to the identified target sequence.

Detection, Identification and/or Quantitation:

By detection is meant analysis for the presence or absence of the organism optionally present in the sample. By identification is meant establishment of the identity of the organism by taxon, for example, genus and/or species name. By quantitation is meant enumeration of the organisms in a sample. The term identification is meant to include either or both detection and quantification. Some assay formats provide simultaneous detection, identification and quantitation (for example see Stender, H. et al., *J. Microbiol. Methods.* 45:31-39 (2001), others provide detection and identification (for example see Stender, H. et al., *Int. J. Tuberc. Lung Dis.* 3:830-837 (1999) and yet other assay formats just provide identification (for example see Oliveira, K et al. *J. Clin. Microbiol.* 40:247-251 (2002)).

Antibiotic Resistance

By determination of resistance to antibiotics is meant analysis of an organisms susceptibility to antibiotics based on specific genes or mutations associated with resistance or susceptibility to antimicrobial agents.

II. Preferred Embodiments of the Invention a. PNA Probes:

In one embodiment, the PNA probes of this invention are suitable for identifying microorganisms. General characteristics (e.g. length, labels, nucleobase sequences, linkers etc.) of PNA probes suitable for the analysis have been previously described herein. The preferred probing nucleobase sequence of PNA probes of this invention are listed in Table 1.

TABLE 1

| Sequence ID | Nucleobase sequence |
| --- | --- |
| Seq. Id. No. 1 | CAC-CCT-CTC-AGG |
| Seq. Id. No. 2 | TCC-TCT-CAG-ACC |
| Seq. Id. No. 3 | TCC-TCT-CDG-DCC |
| Seq. Id. No. 4 | CCC-TAG-TCG-GCA-TAG |
| Seq. Id. No. 5 | CCA-AGA-GAT-CCG-TTG |

The PNA probes of this invention may comprise only a probing nucleobase sequence (as previously described herein) or may comprise additional moieties. Non-limiting examples of additional moieties include detectable moieties (labels), linkers, spacers, natural or non-natural amino acids, or other subunits of PNA, DNA or RNA. Additional moieties may be functional or non-functional in an assay. Generally however, additional moieties will be selected to be functional within the design of the assay in which the PNA probe is to be used. The preferred PNA probes of this invention are labeled with one or more detectable moieties selected from the group consisting of fluorophores, enzymes and haptens.

Probes of the invention may be modified through incorporation of bases with enabling properties. Modifications may be in the form of enhancements/changes to the base-pairing properties of the probe. For example the modified adenine analog, 2,6-diaminopurine can be added to a PNA probe to increase its Tm. Increases of 1-3 degrees (centigrade) have been observed for each 2,6-diaminopurine substitution. Modifications may be to the non-pairing portion of the molecules, such as at the probe termini, in the form of moieties to enhance, for example, solubility of the probe. Modifications can also be made to the pseudopeptide backbone of the probe. Such modifications may introduce advantageous properties to the probe for instance by introducing handedness/chirality to the probe, or by introducing internal sites for the addition of solubility enhancers or labels, or both. An example of a modification to the pseudopeptide backbone is the so called Gamma substitutions exemplified in Englund and Appella (*Org. Letters,* 2005). Such modifications are made at position K as shown in Formula 1.

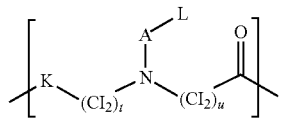

In preferred embodiments, the probes of this invention are used in in situ hybridization (ISH) and fluorescence in situ hybridization (FISH) assays. Excess probe used in an ISH or FISH assay typically must be removed so that the detectable moiety of the specifically bound probe can be detected above the background signal that results from still present but unhybridized probe. Generally, the excess probe is washed away after the sample has been incubated with probe for a period of time. However, the use of self-indicating probes is a preferred embodiment of this invention, since there is no requirement that excess self-indicating probe be completely removed (washed away) from the sample since it generates little or no detectable background. In addition to ISH or FISH assays, self-indicating probes comprising the selected probing nucleobase sequence described herein are particularly useful in all kinds of homogeneous assays such as in real-time PCR or useful with self-indicating devices (e.g. lateral flow assay) or self-indicating arrays.

b. PNA Probe Sets and Use

Probe sets of this invention comprise two of more PNA probes. In one embodiment, some of the PNA probes of the set can be blocking probes. Probes sets may include any group of two or more of the probes of this invention, and may be labeled or non-labeled, and may also include probes not specifically described here, but which include at least one of the probes of this invention.

In certain embodiments, the present invention features probe sets comprising Seq Id. No. 1 and Seq Id. No. 2.

In other embodiments, the present invention features probe sets comprising Seq Id. No. 1 and/or Seq Id. No. 2 in combination with Seq Id. No. 4 and/or Seq Id. No. 5 (e.g. Seq Id No. 1 and Seq Id. No. 4, or Seq Id No. 1 and Seq Id. No. 5, or Seq Id No. 2 and Seq Id. No. 4, or Seq Id No. 2 and Seq Id. No. 5, or Seq Id. No. 1, Seq Id. No. 4 and Seq Id. No. 5, or Seq Id. No. 1, Seq Id. No. 2, Seq Id. No. 4 and Seq Id. No. 5, or Seq Id. No. 2, Seq Id. No. 4 and Seq Id. No. 5).

The probes described herein may be labelled with one ore more 2,6-diaminopurine residue(s).

In other certain embodiments, the present invention features probe sets comprising Seq Id. No. 1 and Seq Id. No. 3.

In other further embodiments, the present invention features probe sets comprising Seq Id. No. 1 and/or Seq Id. No. 3 in combination with Seq Id. No. 4 and/or Seq Id. No. 5 (e.g. Seq Id. No. 1 and Seq Id. No. 4, or Seq Id. No. 1 and Seq Id. No. 5, or Seq Id. No. 3 and Seq Id. No. 4, or Seq Id. No. 3 and Seq Id. No. 5, or Seq Id. No. 1, Seq Id. No. 4 and Seq Id. No. 5, or Seq Id. No. 3, Seq Id. No. 4 and Seq Id. No. 5, or Seq Id. No. 1, Seq Id. No. 3, Seq Id. No. 4 and Seq Id. No. 5).

In further exemplary embodiments, any of the above probes may be labelled. For example, a Gram positive probe contains a fluorescein labeled dye and a Gram negative probe contains a Tamra labeled dye. In another related embodiment, the yeast/fungi probes are preferably triple labeled probes made up of two fluoresceins and one Tamra dye.

Accordingly, Gram-positive organisms produce green fluorescence, Gram-negative organisms produce red fluorescence, and fungi produce lemon-yellow fluorescence.

c. Methods:

In another embodiment, this invention is directed to a method suitable for analysis of microorganisms optionally in a sample. The general and specific characteristics of PNA probes suitable for the analysis of microorganisms have been previously described herein. Preferred probing nucleobase sequences are listed in Table 1.

The present invention is the first time that differentiation of Gram types has been carried out using PNA probes.

The method for analysis of microorganisms in a sample comprises contacting the sample with one or more PNA probes suitable for hybridization to a target sequence which is specific.

According to the method, the microorganism in the sample is then identified, detected, and/or quantitated or its resistance to antibiotics is determined. This is made possible by correlating hybridization, under suitable hybridization conditions, of the probing nucleobase sequence of a PNA probe to the target sequence of microorganism sought to be detected with the presence, absence or number of the microorganisms in the sample. Typically, this correlation is made possible by direct or indirect detection of the probe/target sequence hybrid.

In related embodiments, the method may include contacting the sample with another probe for signal amplification or detection of one or more other species.

Fluorescence in situ Hybridization and Real-time PCR:

The PNA probes, methods, kits and compositions of this invention are particularly useful for the rapid probe-based analysis of microorganisms. In preferred embodiments, in situ hybridization or PCR is used as the assay format for analysis of microorganisms. Most preferably, fluorescence in situ hybridization (PNA FISH) or real-time PCR is the assay format. (Reviewed by Stender et al. *J. Microbiol. Methods* 48:1-17 (2002)). Preferably, smears for PNA FISH analysis are not treated with cross-linking agents or enzymes prior to hybridization.

Exemplary Assay Formats:

Exemplary methods for performing PNA FISH can be found in: Oliveira et., *J. Clin. Microbiol* 40:247-251 (2002), Rigby et al., *J. Clin. Microbiol.* 40:2182-2186 (2002), Stender et al., *J. Clin. Microbiol.* 37:2760-2765 (1999), Perry-O'Keefe et al., *J. Microbiol. Methods* 47:281-292 (2001). According to one method, a smear of the sample, such as, but not limited to, a positive blood culture, is prepared on microscope slides and covered with one drop of the fluorescein-labeled PNA probe in hybridization buffer. A coverslip is placed on the smear to ensure an even coverage, and the slide is subsequently placed on a slide warmer or incubator at 55° C. for 90 minutes. Following hybridization, the coverslip is removed by submerging the slide into a pre-warmed stringent wash solution and the slide is washed for 30 minutes. The smear is finally mounted with one drop of mounting fluid, covered with a coverslip and examined by fluorescence microscopy.

Microorganisms optimally present in a sample which may be analyzed with the PNA probes contained in the kits of this invention can be determined by several instruments, such as but not limited to the following examples: microscope (for example see Oliveira et al., *J. Clin. Microbiol* 40:247-251 (2002)), film (for example see Perry-O'Keefe et al., *J. Appl. Microbiol.* 90:180-189) (2001), camera and instant film (for example see Stender et al., *J. Microbiol. Methods* 42:245-253 (2000)), luminometer (for example see Stender et al., *J. Microbiol. Methods* 46:69-75 (2001), laser scanning device (for example see Stender et al., *J. Microbiol. Methods* 45: 31-39 (2001) or flow cytometer (for example see Wordon et al., *Appl. Environ. Microbiol.* 66:284-289 (2000)). Automated slide scanners and flow cytometers are particularly useful for rapidly quantitating the number of microorganisms present in a sample of interest.

Exemplary methods for performing real-time PCR using self-reporting PNA probes can be found in: Fiandaca et al., Abstract, Nucleic Acid-Based technologies. DNA/RNA/

PNA Diagnostics, Washington, D.C., May 14-16, 2001, and Perry-O'Keefe et al., Abstract, International Conference on Emerging Infectious Diseases, Atlanta, 2002.

d. Kits:

In yet another embodiment, this invention is directed to kits suitable for performing an assay, which analyses microorganisms optionally present in a sample. The general and preferred characteristics of PNA probes suitable for the analysis of microorganisms have been previously described herein. Preferred probing nucleobase sequences are listed in Table 1. Furthermore, methods suitable for using the PNA probes to analyse microorganisms in a sample have been previously described herein.

The kits of this invention comprise one or more PNA probes and other reagents or compositions which are selected to perform an assay or otherwise simplify the performance of an assay used to analyze microorganisms in a sample.

e. Exemplary Applications for Using the Invention:

The PNA probes, methods and kits of this invention are particularly useful for the analysis of microorganisms in clinical samples, e.g. urine, blood, wounds, sputum, laryngeal swabs, gastric lavage, bronchial washings, blood culture, bronchoalveolar lavage, biopsies, aspirates, expectorates as well as in food, beverages, water, pharmaceutical products, personal care products, dairy products or environmental samples and cultures thereof.

Additional Detection Strategies

Though probes labeled with fluorescein and tamra are described, it is within the concept of this invention that any combination of fluorescent labels could be used which produce a perceivable third color. Likewise, use of two or more labels to produce multiple perceivable colors is also envisioned. Potential fluorescent labels are included in the description. Coincidental fluorescence of two or more fluorescent moieties has been demonstrated to be useful in the generation of a spectrum of colors (Kool et al JACS 2003). Combination colors are made through "mixtures" of two or more fluorophores, and adjustment of their ratios. For example, a combination of two parts red and one part green produces a different color that one part red and two parts green. Though accurate discrimination of these various shades by eye may have a practical limit, it is not difficult to conceive of a device which could accurately perceive such subtle color variations.

Detectable and Independently Detectable Moieties/Multiplex Analysis:

A multiplex hybridization assay can be performed in accordance with embodiments of the present invention. In a multiplex assay, numerous conditions of interest can be simultaneously examined.

Multiplex analysis relies on the ability to sort sample components or the data associated therewith, during or after the assay is completed. In preferred embodiments of the invention, one or more distinct independently detectable moieties can be used to label two or more different probes used in an assay. The ability to differentiate between and/or quantitate each of the independently detectable moieties provides the means to multiplex a hybridization assay. Correlation of the hybridization of each of the distinctly (independently) labeled probes to particular nucleic acid sequences is indicative of presence, absence or quantity of each organism sought to be detected in the sample.

Consequently, the multiplex assays of this invention can be used to simultaneously detect the presence, absence or quantity of two or more different organisms (e.g. species of Klebsiella) in the same sample and in the same assay. For example, a multiplex assay may utilize two or more PNA probes, each being labeled with an independently detectable fluorophore, or a set of independently detectable fluorophores.

Accordingly, the invention provides for a method to treat a patient which in embodiment includes at least one of and preferably all of the following steps:

a) obtaining a biological sample from the patient b) identifying one or more microorganisms in the sample; and c) administering at least one antibiotic with activity towards elimination of the infection.

As described herein, the term "identifying" is meant to include either or both detection and quantitation.

The invention further provides for a PNA probe set that includes at least one of the PNA probes provided herein, preferably two or more probes, wherein the probes make a third color by coincidental fluorescence.

Also included in the method of the invention is optionally another probe for signal amplification or detection of one or more other species.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLES

Example 1—Comparison of PNA Probes with and without 2,6-diaminopurine Residues (D)

An experiment was performed to measure the relative signal strength of probes which contain only adenine (A) PNA residues, and probes which contain 2,6-diaminopurine residues (D) in place of adenine residues.

Tryptic soy agar cultures were prepared for each of four Gram negative organisms, Acinetobacter baumanii, Enterobacter cloacae, Klebsiella pneumoniae, and Pseudomonas aeruginosa. Individual liquid cultures (1 mL of sterile blood in blood culture media) were inoculated and incubated at 37° C. for 1.5 to 3 hours with shaking. Smears were prepared on glass slides by combining 10 uL of culture to 1 drop of GN Fixation Solution (AdvanDx, Woburn, Mass.), then heated at 55° C. until the smear was dry.

Probe solutions were individually prepared in Hybridization Buffer at 500 nM of a universal bacterial probe (Seq. Id No. 7), the probe without 2,6 diaminopurine residues (Seq. Id No. 2), a probe with one 2,6-diaminopurine residue at position 10 (Seq. Id No. 6), and a probe with two 2,6-diaminopurine residues at positions 8 and 10 (Seq. Id No. 3). All probes were labeled with tetramethylrhodamine.

1 drop of probe solution was added to each slide, a coverslip was placed over the drop, and slides were incubated at 55° C. for 30 minutes. Next, slides were washed in 1×PNA FISH Wash Solution (AdvanDx, Woburn, Mass.) at 55° C. for 30 minutes. Slides were mounted with 1 drop PNA FISH Mounting Media (AdvanDx, Woburn, Mass.) and a coverslip was applied. Slides were viewed on a fluorescent microscope with a dual band filter and a 60× oil objective. Slides were scored 0, 1, 2, or 3 where 0=no fluorescence, and 3=bright fluorescence. Results are score in Table 2.

TABLE 2

| Organism | Seq. Id No. 7 | Seq. Id No. 2 | Seq. Id No. 6 | Seq. Id No. 3 |
|---|---|---|---|---|
| Acinetobacter baumanii | 3 | 2 | 3 | 3 |
| Enterobacter cloacae | 3 | 2 | 2 | 3 |
| Klebsiella pneumoniae | 3 | 2 | 2 | 3 |
| Pseudomonas aeruginosa | 2 | 2 | 2 | 2 |

With reference to Table 2, the strength of the fluorescence signal for each organism probed with the universal bacterial probe (Seq. Id No. 7) was scored 3 for all organisms, except *P. aeruginosa*, which scored 2. Comparing the three probes containing zero, one or two 2,6-diaminopurine residues (Seq. Id No. 2, Seq. Id No. 6, Seq. Id No. 3 respectively), there is a trend towards increasingly bright signal with more 2,6-diaminopurine substitutions.

Example 2—Evaluation of Tri-Color Gram-Stain by PNA FISH

Reference strains with inherently known Gram-type were tested by PNA FISH as described above using a mixture of the following PNA probes in the various concentrations:

Tam-TCCTCTCDGDCC (Seq Id No. 3): 250 nM

Flu-CACCCTCTCAGG (Seq Id No. 1): 500 nM

Tam-CCCTAGTCGGCATAG-Lys(Flu)-Lys(Flu) (Seq Id No. 4): 100 nM

Tam-CCAAGAGATCCGTTG-Lys(Flu)-Lys(Flu) (Seq Id No. 5): 100 nM

The Gram positive and Gram negative probes target the 16S rRNA and overlap in the same region. The Gram positive probe contains a fluorescein labeled dye and the Gram negative probe contains a Tamra labeled dye. The yeast/fungi probes targets the 18S and 5.8S rRNAs and are triple labeled probes made up of two fluoresceins and one Tamra dye.

Gram-positive organisms produce green fluorescence, Gram-negative organisms produce red fluorescence, and fungi produce lemon-yellow fluorescence. In addition to fluorescence, cell morphology may also be observed.

In some experiments mixtures of individually labeled PNA probes of Seq. 4 and 5 were used and produced a less preferred more orange color.

Results from testing more than 100 reference strains, including 58 aerobic species (Table 3; Table 4), 20 fungal species (Table 5) spanning four taxonomic orders, and 8 obligate anaerobic species (Table 6) are shown below.

*Klebsiella*, *Acinetobacter*, and *Haemophilus* are common Gram negative pathogens isolated from blood cultures and known to stain as Gram variable. However, Gram Traffic Light PNA FISH correctly identifies these organisms as Gram negative.

TABLE 3

Gram Positive Organisms (aerobic)

| Organism | Sample ID | Color/Morphology |
|---|---|---|
| Bacillus cereus | ATCC 10876 | Green. Rods. |
| Bacillus sphaericus | ATCC 4525 | Green. Rods. |
| Corynebacterium renale | ATCC 19412 | Green. Rods. |
| Enterococcus casseliflavus | ATCC 25788 | Green cocci. Pairs. |
| Enterococcus columbae | ATCC 51263 | Green cocci. Chains. |
| Enterococcus durans | ATCC 11576 | Green cocci. Chains. |
| Enterococcus faecalis | ATCC 49452 | Green cocci. Pairs. Chains. |
| Enterococcus faecalis | ATCC 7080 | Green cocci. Pairs. Chains. |
| Enterococcus faecalis | NCTC 775 | Green cocci. Pairs. Chains. |
| Enterococcus faecalis | ATCC 14506 | Green cocci. Pairs. Chains. |
| Enterococcus faecalis | NCTC 13379 | Green cocci. Pairs. Chains. |
| Enterococcus faecalis | ATCC 29212 | Green cocci. Clusters. |
| Enterococcus faecium | ATCC 51858 | Green cocci. Chains. |
| Enterococcus hirae | ATCC 10541 | Green cocci. Chains. |
| Enterococcus malodoratus | ATCC 43197 | Green cocci. Pairs. Chains. |
| Enterococcus raffinosus | ATCC 49464 | Green cocci. Pairs. Chains. |
| Enterococcus saccharolyticus | ATCC 43076 | Green cocci. Chains. |
| Staphylococcus aureus | ATCC 29213 | Green cocci. Pairs. Chains. |
| Staphylococcus capitis | ATCC 35661 | Green cocci. |
| Staphylococcus epidermidis | ATCC 14990 | Green cocci. Clusters. |
| Staphylococcus gallinarum | ATCC 700401 | Green cocci. Clusters. |
| Staphylococcus lugdunensis | ATCC 700328 | Green cocci. Clusters. |
| Staphylococcus schleiferi subsp schleiferi | ATCC 43808 | Green cocci. Clusters. |
| Staphylococcus sciuri subsp. sciuri | ATCC 29061 | Green cocci. Clusters. |
| Staphylococcus simulans | ATCC 27851 | Green cocci. Clusters. |
| Staphylococcus warneri | ATCC 49454 | Green cocci. Clusters. |
| Staphylococcus xylosus | ATCC 29971 | Green cocci. Clusters. |
| Streptococcus intermedius | ATCC 9895 | Green cocci. Chains. |
| Streptococcus agalactiae | ATCC 13813 | Green cocci. Chains. |
| Streptococcus bovis | ATCC 33317 | Green cocci. Chains. |
| Streptococcus iniae | ATCC 29178 | Green cocci. Chains. |
| Streptococcus oralis | ATCC 9811 | Green cocci. Chains. |
| Streptococcus phocae | ATCC 51973 | Green cocci. Chains. |
| Streptococcus pyogenes | ATCC 12384 | Green cocci. Chains. |
| Streptococcus thoraltensis | ATCC 700865 | Green cocci. Chains. |
| Streptococcus uberis | ATCC 9927 | Green cocci. Chains |

TABLE 4

Gram Negative Organisms (aerobic)

| Organism | Sample ID# | Color/Morphology |
|---|---|---|
| Moraxella catarrhalis | ATCC 25240 | Red. Diplococci. |
| Acinetobacter baumannii | ATCC 19606 | Red. Rods. |
| Acinetobacter calcoaceticus | ATCC 51432 | Red. Rods. |
| Acinetobacter haemolyticus | ATCC 17906 | Red. Rods. |
| Acinetobacter junii | ATCC 17908 | Red. Rods. |
| Acinetobacter radioresistens | ATCC 43998 | Red. Rods. |
| Aeromonas hydrophila | ATCC 49140 | Red. Rods. |

TABLE 4-continued

Gram Negative Organisms (aerobic)

| Organism | Sample ID# | Color/Morphology |
|---|---|---|
| Cardiobacterium hominis | ATCC 14900 | Red. Rods. |
| Eikenella corrodens | ATCC 23834 | Red. Rods. |
| Enterobacter aerogenes | ATCC 29010 | Red. Rods. |
| Enterobacter aerogenes | ATCC 49469 | Red. Rods. |
| Enterobacter cloacae | ATCC 13047 | Red. Rods. |
| Enterobacter cloacae | ATCC 13047 | Red. Rods. |
| Enterobacter cloacae | ATCC 13047 | Red. Rods. |
| Escherichia coli | ATCC 35218 | Red. Rods. |
| Escherichia coli | ATCC 35218 | Red. Rods. |
| Fusobacterium nucleatum | ATCC 25586 | Green*. Rods, thread-like. |
| Haemophilus influenza | ATCC 33533 | Red. Rods. |
| Klebsiella oxytoca | ATCC 43086 | Red. Rods. |
| Klebsiella pneumoniae | ATCC 13882 | Red. Rods. |
| Providencia stuartii | ATCC 33672 | Red. Rods. |
| Pseudomonas aeruginosa | ATCC 10145 | Red. Rods. |
| Pseudomonas aeruginosa | ATCC 10145 | Red. Rods. |
| Pseudomonas aeruginosa | ATCC 10145 | Red. Rods. |
| Pseudomonas fluorescens | ATCC 15553 | Red. Rods. |
| Pseudomonas fluorescens | ATCC 17563 | Red. Rods. |
| Pseudomonas putida | ATCC 49128 | Red. Rods. |
| Pseudomonas stutzeri | ATCC 17588 | Red. Rods. |
| Pseudomonas stutzeri | ATCC 17587 | Red. Rods. |
| Pseudomonas stutzeri | ATCC 17591 | Red. Rods. |
| Raoultella terrigena | ATCC 33257 | Red. Rods. |
| Raoutella planticola | ATCC 33558 | Red. Rods. |
| Salmonella enterica subsp enterica | No ID# | Red. Rods. |
| Serratia marcescens | ATCC 14756 | Red. Rods. |
| Shigella boydii | ATCC 35966 | Red. Rods. |
| Stenotrophomonas maltophilia | ATCC 13636 | Red. Rods. |
| Stenotrophomonas maltophilia | ATCC 49130 | Red. Rods. |
| Vibrio vulnificus | ATCC 27562 | Red. Rods, curved. |

*Incorrect Gram result by PNA FISH based on known Gram stain classification.

TABLE 5

Fungi

| Organism | Sample ID# | Color |
|---|---|---|
| Aspergillus terreus | No ID# | Lemon-yellow. |
| Aspergillus versicolor | No ID# | Lemon-yellow. |
| Candida albicans | ATCC 14053 | Lemon-yellow. |
| Candida albicans | NRRL Y-27022 | Lemon-yellow. |
| Candida glabrata | ATCC 64677 | Lemon-yellow. |
| Candida guilliermondii | ATCC 34134 | Orange*. |
| Candida inconspicua | ATCC 16783 | Orange*. |
| Candida kefyr | ATCC 4135 | Orange*. |
| Candida krusei | ATCC 14243 | Orange*. |
| Candida lusitaniae | ATCC 66035 | Orange*. |
| Candida orthopsilosis | Clinical Isolate | Orange*. |
| Candida parapsilosis | NRRL YB-415 | Orange*. |
| Candida sojae | NRRL Y-17909 | Orange*. |
| Candida tropicalis | ATCC 13803 | Lemon-yellow. |
| Candida viswanathii | NRRL Y-27370 | Orange*. |
| Candida zeylanoides | NRRL Y-1774 | Orange*. |
| Cryptococcus neoformans | ATCC 204092 | Orange*. |
| Gliocladium viride | No ID# | Lemon-yellow. |
| Paecilomyces lilacinus | No ID# | Lemon-yellow. |
| Penicillium griseofulvum | No ID# | Lemon-yellow. |
| Saccharomyces cerevisiae | ATCC 9763 | Orange*. |

*Some strains were tested using mixtures of PanFungal probes which were singly labeled with Flu or Tam and produced a less appealing orange fluorescence. Triple-labeled probes described above produce lemon-yellow fluorescence.

TABLE 6

Anaerobes

| Organism | Sample ID# | Color/Morphology |
|---|---|---|
| Bacteroides fragilis | ATCC 23745 | Red. Rods. |
| Bacteroides uniformis | ATCC 8492 | Red. Rods. |
| Finegoldia magna | ATCC 29328 | Red*. cocci. |
| Parvimonas micra (Micromonas micros) | ATCC 33270 | Red*. cocci. |
| PeptoStreptococcus anaerobius | ATCC 27337 | Green. cocci. |
| Prevotella intermedia | ATCC 15032 | Red. Rods. |
| Propionibacterium acnes | ATCC 11827 | Green. Rods. |

*Incorrect Gram result by PNA FISH based on known Gram stain classification.

In summary, Gram stain result by PNA FISH provided the correct results relative to known Gram stain classification, except for *Fusobacterium nucleatum* (Gram-negative) which was identified as Gram positive. *Finegoldia magna* and *Parvimonas micra* (*Micromonas micros*), 2 Gram positive anaerobic species which rarely occur in blood culture, were identified as Gram negative. Upon in silico sequence analysis of these three organisms, the cross-reaction is an expected result. Further, the cross reaction of these organisms is not a function of their anaerobic phenotype, they just happen to be anaerobic. A few offshoots of the bacteria kingdom which will produce the wrong result in this test (when examined in silico) have been identified. Those are either in the Fusobacteria phylum (being identified as Gram-positive) or the family called Clostridiales Family XI. *Incertae Sedis*, (being identified as Gram negative). Clostridiales Family XI does not include the *Clostridium* genus.

Example 3—Testing of Routine Blood Cultures 74 routine positive blood cultures were analyzed using the tri-color PNA FISH assay set forth above. Results by PNA FISH were compared against the routine Gram stain and species identification reports provided by the clinical laboratory. 12 of 12 Gram-negative rods, 63 of 63 Gram-positive cocci, 2 of 2 Gram positive rods, and 1 of 1 yeast were correctly identified. In addition, the assay correctly identified 6 Gram negative rods and 1 Gram-positive rod initially reported as Gram variable rods.

Example 4—Parallel Testing and Reporting of Gram Type and Species Identity

Four routine, positive blood culture samples were analyzed in parallel by the tri-color PNA FISH for Gram typing described above and by *E. faecalis*/OE PNA (KT 003), GNR Traffic Light PNA (KT 011), Yeast Traffic Light PNA (KT 009), and *S. aureus*/CNS PNA (KT 005) (AdvanDx, Woburn, Mass.).

The results of the Gram stain was used to guide which slide to be viewed for species identification as outlined in Flow chart A.

Flow-Chart A (FIG. 1): Determining Species Specific PNA FISH Slide Selection

The results by PNA FISH were in 100% agreement with results obtained by routine identification as outlined in Table 7.

TABLE 7

Results of Clinical Sample Testing

| | | Clinical Sample | | | |
|---|---|---|---|---|---|
| | | LC 1028 | LC 1029 | LC 1030 | LC 1031 |
| Routine | Gram Stain Report | GPC chains. | GPC clusters. | GNR. | GNR. |
| | Species Identification | α-Hemolytic Strep Viridans | Staphylococcus aureus | Escherichia coli (probable) | Escherichia coli (probable) |
| PNA FISH | Gram Stain Report | GPC chains | GPC clusters | GNR | GNR |
| | Species Identification | Negative | S. aureus | E. coli | E. coli |

*Routine Gram Stain Results provided by Lahey Clinic (Burlington, MA).

In summary, the parallel testing provide Gram stain and species identification within the same assay format and thus allow both results to be reported simultaneously and without delay.

Example 5

An experiment was designed to test individual probes in the FISH format. With the exception of the probe solutions, the experiment was performed as in Example 1. Probe solutions were prepared as follows, Seq Id No. 1 (fluorescein labeled), 500 nM; Seq Id No. 2 (tetramethylrhodamine labeled), 250 nM; or Seq Id No. 3 (tetramethylrhodamine labeled), 250 nM. Slides were scored by color, and given a value of 0, 1, 2, or 3 where 0=no fluorescence, and 3=bright fluorescence. Data are displayed in Table 8.

TABLE 8

| Organism | Strain ID | Result Seq ID #1 | Result Seq ID #2 | Result Seq ID #3 |
|---|---|---|---|---|
| Escherichia coli | ATCC 35218 | 0 | 2, red | 3, red |
| Enterococcus faecalis | ATCC 29212 | 3, green | 0 | 0 |
| Pseudomonas aeruginosa | ATCC 10145 | 0 | 2, red | 3, red |
| Staphylococcus aureus | ATCC 29213 | 3, green | 1, red | 2, red |
| Staphylococcus epidermidis | ATCC 14990 | 3, green | 0 | 2, red |

The experiment demonstrates that the Gram-negative "specific" probes (SeqID#2 and SeqID.#3) cross react with some Gram-positive organisms when used individually in a hybridization reaction.

Example 6—Evaluation of Tri-Color Gram-Stain by QuickFISH

The Gram Traffic Light PNA FISH method was tested using the "QuickFISH" assay method. QuickFISH is similar to PNA FISH, in that PNA probes are used to detect rRNA targets in microorganisms. Unlike PNA FISH, QuickFISH uses a "self-reporting" probe system, in which quencher-labeled complementary sequences are added to the hybridization mixture. The quencher sequences bind to any fluorescent PNA which is not hybridized to rRNA after the hybridization step, quenching their fluorescence. Since fluorescent-labeled probes are only detectable when bound to rRNA sequences the test does not require a wash step (as is typical in FISH assays) to remove excess fluorescent-labeled probe.

The Gram Traffic Light QuickFISH test was used to screen samples to evaluate the test's performance. Samples included simulated blood cultures, hospital blood cultures (sub-aliquots of actual blood cultures from human patients) and bronchial alveolar lavage (BAL) samples (sub-aliquots of actual BALs from human patients). Smears of hospital blood cultures were prepared on glass slides by adding 1 drop of QuickFix-1 fixation solution (AdvanDx, Woburn, Mass.), followed by 10 uL of culture then heated at 55° C. until the smear was dry (2-4 minutes). The fixation was completed by adding 2 drops of QuickFix-2 fixation solution (AdvanDx, Woburn, Mass.). For simulated blood cultures, the same fixation method was used. For simulated blood cultures, individual liquid cultures (1 mL of a blood culture media spiked with sterile human donor blood) were inoculated with one colony of cells from a freshly prepared agar plate and incubated at 37° C. for 1.5 to 18 hours with shaking. For hospital BAL cultures, samples were first passed through a 30 um pore filter. Fixation was performed by adding 2 drops of QuickFix-2 to the slide at 55° C. and dried (about 1 minute). Next 10 uL of BAL sample was applied to the slide (over the dried reagent) and spread to dry at 55° C. (about 2 minutes), then a third drop of QuickFix-2 was applied on top of the dried sample and allowed to dry at 55° C. (about 1 minute).

For the QuickFISH test, Gram-positive, Gram-negative and pan-fungal probes were used similar to those described above. An additional probe specific for certain coagulase negative staphylococci was added to improve the signal strength of some coagulase negative staphylococci strains.

2 drops of probe solution were added a coverslip, mixed with a plastic wand, then the coverslip was placed on the sample, and slides were incubated at 55° C. for 15 minutes. Slides were viewed on a fluorescent microscope with a dual band filter and a 60× oil objective. Slides were scored by the color of the fluorescence from the cells.

The hybridization reagent contained N-(2-hydroxyethyl) piperazine-N'-(4-butanesulfonic acid, salts, polyamino carboxylic acid, polyethylene glycol, formamide, nonionic surfactant, a dye, e.g. an azo dye, and a small molecule dye compound.

The probe sequences used for Gram Traffic Light QuickFISH are listed below. Preferably, each probe has two quenchers.

```
                                             Seq Id. No. 1
  A  Flu-CACCCTCTCAGG

Seq Id. No. 2
  B  Ac-TCCTCTCAGACC-Lys(Tam)

Seq Id. No. 3
  C  Tam-CCCTAGTCGGCATAG-Lys(Flu)-Lys(Flu)
```

A fourth probe listed below was also added to boost the signal strength of certain Staphylococcus species.

```
                                            (Seq Id. No. 6)
               Flu-AGACGTGCATAGT
```

The PNAs were used at the following concentrations (all in nM) A, 300; B, 150; C, 100.

The Gram Traffic Light QuickFISH test was performed on 66 blood culture samples including 52 reference strains in simulated blood cultures and 14 fresh blood culture samples obtained from a hospital. Simulated blood cultures included 19 Gram-positive strains, 5 Gram-negative strains and 28 fungi strains. All samples tested gave the expected result when compared to routine Gram stain. All data are depicted in tables 9 and 10 below.

Gram Traffic Light QuickFISH was also tested on BAL samples. Fourteen clinical samples were obtained and tested. The results agreed with traditional Gram-stain performed immediately prior to the Gram Traffic Light QuickFISH test, and with the hospital identification (ID). Samples included 2 containing Gram-positive organisms, 2 containing Gram-negative organisms, 2 containing yeast, and 2 containing mixed Gram-positive and Gram-negative organisms. The remaining 6 samples were negative for the growth of microorganisms and gave a negative result by Gram Traffic Light QuickFISH and traditional Gram-stain. This data are listed in Table 11.

In certain embodiments of the method, there may optionally be another probe for signal amplification or detection of other species.

TABLE 9

Screening of microbial strains grown in simulated blood culture

| Species | Traditional Gram Stain | Strain ID | Result Color |
|---|---|---|---|
| Staphylococcus aureus | Gram Positive | ATCC 29213 | Green |
| Staphylococcus epidermidis | Gram Positive | ATCC 14990 | Green |
| Staphylococcus xylosus | Gram Positive | ATCC 29974 | Green |
| Enterococcus faecalis | Gram Positive | ATCC 51299 | Green |
| Streptococcus pyogenes | Gram Positive | ATCC 12384 | Green |
| Micrococcus luteus | Gram Positive | ATCC 10240 | Green |
| Enterococcus faecium | Gram Positive | ATCC 27270 | Green |
| Streptococcus uberis | Gram Positive | ATCC 9927 | Green |
| Staphylococcus lugdunensis | Gram Positive | ATCC 700328 | Green |
| Streptococcus salivarius | Gram Positive | ATCC 13419 | Green |
| Staphylococcus lentus | Gram Positive | ATCC 700403 | Green |
| Staphylococcus saprophyticus | Gram Positive | ATCC 15305 | Green |
| Staphylococcus hominis | Gram Positive | ATCC 27844 | Green |
| Staphylococcus warneri | Gram Positive | ATCC 49454 | Green |
| Streptococcus mutans | Gram Positive | ATCC 25175 | Green |
| Staphylococcus schleiferi | Gram Positive | ATCC 43808 | Green |
| Streptococcus anginosis | Gram Positive | ATCC 33297 | Green |
| Staphylococcus auricularis | Gram Positive | ATCC 33753 | Green |
| Staphylococcus haemolyticus | Gram Positive | ATCC 29970 | Green |
| Pseudomonas aeruginosa | Gram Negative | ATCC 10145 | Red |
| Klebsiella oxytoca | Gram Negative | ATCC 43086 | Red |
| Klebsiella pneumoniae | Gram Negative | ATCC 13882 | Red |
| Acinetobacter baumannii | Gram Negative | ATCC 19606 | Red |
| Escherichia coli | Gram Negative | ATCC 35218 | Red |
| Candida parapsilosis | Yeast | YB415 | Yellow |
| Candida glabrata | Yeast | ATCC 15126 | Yellow |
| Candida krusei | Yeast | ATCC 14243 | Yellow |
| Candida glabrata | Yeast | Clinical isolate | Yellow |
| Candida glabrata | Yeast | ATCC 64677 | Yellow |
| Candida glabrata | Yeast | ATCC 2001 | Yellow |
| Candida glabrata | Yeast | ATCC 15126 | Yellow |
| Candida glabrata | Yeast | Clinical isolate | Yellow |
| Candida glabrata | Yeast | Clinical isolate | Yellow |
| Candida glabrata | Yeast | Clinical isolate | Yellow |
| Candida glabrata | Yeast | ATCC 90030 | Yellow |
| Candida glabrata | Yeast | ATCC 66032 | Yellow |
| Candida dubliniensis | Yeast | 1492 | Yellow |
| Candida bracarensis | Yeast | Clinical isolate | Yellow |
| Candida nivariensis | Yeast | Clinical isolate | Yellow |
| Saccharomyces cerevisiae | Yeast | ATCC 9763 | Yellow |
| Candida orthopsilosis | Yeast | ATCC 96141 | Yellow |
| Candida metapsilosis | Yeast | ATCC 96140 | Yellow |
| Candida tropicalis | Yeast | ATCC 750 | Yellow |
| Candida albicans | Yeast | ATCC 14053 | Yellow |

TABLE 9-continued

Screening of microbial strains grown in simulated blood culture

| Species | Traditional Gram Stain | Strain ID | Result Color |
|---|---|---|---|
| Candida albicans | Yeast | Y-27022 | Yellow |
| Clavispora lusitaniae | Yeast | ATCC 66035 | Yellow |
| Pichia guilliermondii | Yeast | 31134 | Yellow |
| Candida kefyr | Yeast | ATCC 4153 | Yellow |
| Trichosporon mucoides | Yeast | ATCC 201382 | Yellow |
| Fusarium solani | Yeast | ATCC 36031 | Yellow |
| Geotrichum candidum | Yeast | ATCC 34614 | Yellow |
| Malassezia furfur | Yeast | ATCC 14521 | Yellow |

TABLE 10

Screening of hospital blood culture samples

| Sample ID | Hospital ID | Traditional Gram Stain | Result Color |
|---|---|---|---|
| 490 | Coagulase-negative staphylococci | Gram Positive | Green |
| 502 | Enterococcus spp. | Gram Positive | Green |
| 485 | Streptococcus spp. | Gram Positive | Green |
| 503 | Coagulase-negative staphylococci | Gram Positive | Green |
| 501 | Enterococcus spp. | Gram Positive | Green |
| 483 | Enterococcus spp. | Gram Positive | Green |
| 660 | Coagulase-negative staphylococci | Gram Positive | Green |
| 656 | Coagulase-negative staphylococci | Gram Positive | Green |
| 489 | Escherichia coli | Gram Negative | Red |
| 488 | Escherichia coli | Gram Negative | Red |
| 491 | Escherichia coli | Gram Negative | Red |
| 625 | Escherichia coli | Gram Negative | Red |
| 661 | Candida tropicalis | Yeast | Yellow |
| 624 | Yeast (unidentified) | Yeast | Yellow |

TABLE 11

Screening of hospital BAL samples

| Hospital ID | Hospital ID | Traditional Gram Stain | Result Color |
|---|---|---|---|
| 2230 | Staphylococcus aureus | Gram Positive | Green |
| 31332 | Normal Flora | Gram Positive | Green |
| 24665 | Negative | Negative | Negative |
| 16279 | Negative | Negative | Negative |
| 28073 | Negative | Negative | Negative |
| 29716 | Negative | Negative | Negative |
| 29719 | Negative | Negative | Negative |
| 69264 | Negative | Negative | Negative |
| 20203 | Pseudomonas aeruginosa | Gram Negative | Red |
| 19742 | Normal Flora | Gram Negative | Red |
| 29582 | Normal Flora | Gram Positive & Gram Negative | Green, Red |
| 45555 | Yeast | not available | Yellow |
| 32222 | Normal Flora | Gram Positive & Gram Negative | Green, Red |
| 52889 | Normal Flora | Yeast | Yellow |

This example demonstrates the application of the Gram Traffic Light QuickFISH test on simulated blood culture, hospital blood culture and hospital BAL samples.

Inclusion of the additional probe to augment the signal of certain *Staphylococcus* species demonstrates how the core probe set of Gram-positive, Gram-negative and fungal specific probes can be augmented to widen the breadth of the test's specificity and/or increase the fluorescence of particular species. As the test is applied to various samples, it is possible that species will be identified which produce a negative test result. In such a case, it is envisioned that the probe mixture may be augmented with probes specific to an organism or group of organisms which are required to be detected.

INCORPORATION BY REFERENCE

The contents of all references, patents, pending patent applications and published patents, cited throughout this application are hereby expressly incorporated by reference.

EQUIVALENTS

While a number of exemplary aspects and embodiments have been discussed above, those of skill in the art will recognize certain modifications, permutations, additions and sub-combinations thereof. It is therefore intended that the claims are interpreted to include all such modifications, permutations, additions and sub-combinations as are within their true spirit and scope.

What is claimed is:

1. A PNA probe for detection of a Gram positive organism selected from the group consisting of *Bacillus cereus, Bacillus sphaericus, Corynebacterium renale, Enterococcus casseliflavus, Enterococcus columbae, Enterococcus durans, Enterococcus faecalis, Enterococcus faecium, Enterococcus hirae, Enterococcus malodoratus, Enterococcus raffinosus, Enterococcus saccharolyticus, Staphylococcus aureus, Staphylococcus capitis, Staphylococcus epidermidis, Staphylococcus gallinarum, Staphylococcus lugdunensis, Staphylococcus schleiferi, Staphylococcus sciuri, Staphylococcus simulans, Staphylococcus warneri, Staphylococcus xylosus, Streptococcus intermedius, Streptococcus agalactiae, Streptococcus bovis, Streptococcus iniae, Streptococcus oralis, Streptococcus phocae, Streptococcus pyogenes, Streptococcus thoraltensis, Streptococcus uberis, Pepto-Streptococcus anaerobius, Propionibacterium acnes, Micrococcus luteus, Streptococcus salivarius, Staphylococcus lentus, Staphylococcus saprophyticus, Staphylococcus hominis, Streptococcus mutans, Streptococcus anginosis, Staphylococcus auricularis, Staphylococcus haemolyticus*, Coagulase-negative *staphylococci, Enterococcus* spp., and *Streptococcus* spp., wherein the probe is 12 bases in length, and wherein the entire sequence of the probe is at least 83% identical to the entire sequence of SEQ ID NO. 1 or its complement.

2. The PNA probe of claim 1, wherein the entire sequence of the probe is at least 92% identical to the entire sequence of SEQ ID NO. 1 or its complement.

3. The PNA probe of claim 1, wherein the sequence of the probe consists of SEQ ID NO. 1 or its complement.

4. The PNA probe of claim 1, wherein the probe hybridizes with ribosomal RNA (rRNA) of one or more target organisms.

5. The PNA probe of claim 4, wherein the target organism is a Gram positive organism.

6. The PNA probe of claim 1, wherein base at position 3 of the sequence of the probe is C, or wherein base at position 12 of the sequence of the probe is G.

7. The PNA probe of claim 6, wherein base at position 3 of the sequence of the probe is C, and wherein base at position 12 of the sequence of the probe is G.

8. The PNA probe of claim 1, wherein the probe further comprises at least one detectable moiety.

9. The PNA probe of claim 8, wherein the detectable moiety or moieties are selected from the group consisting of a conjugate, a branched detection system, a chromophore, a fluorophore, a spin label, a radioisotope, an enzyme, a hapten, an acridinium ester and a luminescent compound.

10. The PNA probe of claim 8, wherein the probe is a self-reporting probe.

11. The PNA probe of claim 10, wherein the probe is a PNA Linear Beacon.

12. The PNA probe of claim 1, wherein the probe is unlabeled.

13. The PNA probe of claim 1, wherein the probe further comprises a spacer or a linker.

14. A PNA probe set comprising one or more probes, wherein one probe of said probe set is the probe of claim 1.

15. The PNA probe set of claim 14, wherein one probe of said probe set targets a Gram positive organism.

16. The probe set of claim 14, wherein the probe set further comprises a probe comprising SEQ ID NO. 2, or its complement; or a sequence that is at least 50% identical to SEQ ID NO. 2, and wherein the base corresponding to position 1 of SEQ ID NO. 2 is conserved as T and the base corresponding to position 10 of SEQ ID NO. 2 is conserved as A.

17. A kit suitable for performing an assay for analysis of microorganisms in a sample, wherein said kit comprises: a) a PNA probe according to claim 1 and b) directions for use.

18. A method for the detection of the presence or amount of one or more gram positive microorganism selected from the group consisting of *Bacillus cereus, Bacillus sphaericus, Corynebacterium renale, Enterococcus casseliflavus, Enterococcus columbae, Enterococcus durans, Enterococcus faecalis, Enterococcus faecium, Enterococcus hirae, Enterococcus malodoratus, Enterococcus raffinosus, Enterococcus saccharolyticus, Staphylococcus aureus, Staphylococcus capitis, Staphylococcus epidermidis, Staphylococcus gallinarum, Staphylococcus lugdunensis, Staphylococcus schleiferi, Staphylococcus sciuri, Staphylococcus simulans, Staphylococcus warneri, Staphylococcus xylosus, Streptococcus intermedius, Streptococcus agalactiae, Streptococcus bovis, Streptococcus iniae, Streptococcus oralis, Streptococcus phocae, Streptococcus pyogenes, Streptococcus thoraltensis, Streptococcus uberis, Pepto-Streptococcus anaerobius, Propionibacterium acnes, Micrococcus luteus, Streptococcus salivarius, Staphylococcus lentus, Staphylococcus saprophyticus, Staphylococcus hominis, Streptococcus mutans, Streptococcus anginosis, Staphylococcus auricularis, Staphylococcus haemolyticus*, Coagulase-negative *staphylococci*, *Enterococcus* spp., and *Streptococcus* spp., in a biological sample, said method comprising: contacting the sample with one or more PNA probe of claim 1;

and detecting hybridization of the one or more PNA probe to one or more rRNA molecule in the sample, wherein detection of rRNA is indicative of the presence or amount of microorganism in the sample.

19. The method of claim 18, further comprising contacting the sample with one or more additional probe for signal amplification or detection of additional microorganism.

20. The method of claim 19, wherein the one or more additional probe detects a gram negative bacteria.

21. The method of claim 20, wherein the gram negative bacteria is selected from the group consisting of *Enterobacter, Escherichia coli, Fusobacterium, Pseudomonas, Klebsiella, Acinetobacter, Raoultella, Salmonella, Serratia, Shigella, Stenotrophomonas, Vibrio* and *Haemophilus*.

22. The method of claim 19, wherein the one or more additional probe comprises SEQ ID NO. 2, or its complement; or a sequence that is at least 50% identical to SEQ ID NO. 2, and wherein the base corresponding to position 1 of SEQ ID NO. 2 is conserved as T and the base corresponding to position 10 of SEQ ID NO. 2 is conserved as A.

23. The method of claim 18, wherein the gram positive bacteria is selected from the group consisting of *Bacillus, Enterococcus, Staphylococcus*, and *Streptococcus*.

24. The method according to claim 18, wherein the analysis takes place in situ.

25. The method according to claim 18, wherein the analysis is fluorescence in situ hybridization.

26. The method of claim 18, wherein the method is used to detect a nucleic acid comprising a target sequence, wherein said nucleic acid has been synthesized or amplified in a reaction.

27. The method of claim 26 wherein the nucleic acid synthesis or nucleic acid amplification reaction is selected from the group consisting of Polymerase Chain Reaction (PCR), Ligase Chain Reaction (LCR), Strand Displacement Amplification (SDA), Transcription-Mediated Amplification (TMA), Rolling Circle Amplification (RCA) and Q beta replicase.

28. The method of claim 18, wherein the method further comprises adding at least one blocking probe to reduce or eliminate any hybridization of the PNA probe to non-target sequence.

29. The method of claim 18, wherein the target sequence is immobilized to a surface.

30. The method of claim 18, wherein said PNA probe is immobilized to a surface.

31. The method of claim 30, wherein said PNA probe is one component of an array.

32. The method of claim 18, wherein the sample is a biological sample.

33. The method of claim 32, wherein the biological sample is selected from the group consisting of blood, urine, secretion, sweat, bronchoalveolar lavage, sputum, stool, mucous and cultures thereof.

34. A method of treating a subject suffering from an infection comprising: obtaining a biological sample from the subject; detecting the presence of one or more microorganism in the sample according to the method of claim 18; and administering at least one antibiotic with activity towards the one or more microorganism, thereby treating the infection.

\* \* \* \* \*

SEQUENCE LISTING

```
<160> NUMBER OF SEQ ID NOS: 6

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA probe

<400> SEQUENCE: 1
caccctctca gg                                                          12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA probe

<400> SEQUENCE: 2
tcctctcaga cc                                                          12

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      PNA probe
<220> FEATURE:
<221> NAME/KEY: modified_base
<222> LOCATION: (8)..(8)
<223> OTHER INFORMATION: 2,6-diaminopurine base
<220> FEATURE:
<221> NAME/KEY: modified_base
<222> LOCATION: (10)..(10)
<223> OTHER INFORMATION: 2,6-diaminopurine base

<400> SEQUENCE: 3
tcctctcngn cc                                                          12

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      PNA probe

<400> SEQUENCE: 4
ccctagtcgg catag                                                       15

<210> SEQ ID NO 5
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      PNA probe

<400> SEQUENCE: 5
ccaagagatc cgttg                                                    15

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
agacgtgcat agt                                                      13
```